US011002746B2

(12) United States Patent
Suzuki et al.

(10) Patent No.: US 11,002,746 B2
(45) Date of Patent: May 11, 2021

(54) BLOOD ANALYZER AND BLOOD ANALYZING METHOD FOR DETERMINING IF PLASMODIUM INFECTION IS PRESENT

(71) Applicant: Sysmex Corporation, Kobe (JP)

(72) Inventors: Yuhgi Suzuki, Kobe (JP); Takuma Watanabe, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 16/585,982

(22) Filed: Sep. 27, 2019

(65) Prior Publication Data
US 2020/0025778 A1    Jan. 23, 2020

Related U.S. Application Data

(63) Continuation of application No. 15/657,962, filed on Jul. 24, 2017, now Pat. No. 10,451,638.

(30) Foreign Application Priority Data

Jul. 25, 2016  (JP) .............................. JP2016-145834
Jun. 16, 2017  (JP) .............................. JP2017-118936

(51) Int. Cl.
*G01N 33/80*    (2006.01)
*C12Q 1/06*     (2006.01)
(Continued)

(52) U.S. Cl.
CPC .............. *G01N 33/80* (2013.01); *C12Q 1/06* (2013.01); *G01N 1/30* (2013.01); *G01N 15/1429* (2013.01);
(Continued)

(58) Field of Classification Search
CPC ....... G01N 21/6428; G01N 2021/4707; G01N 2021/4709; G01N 2021/4726;
(Continued)

(56) References Cited

U.S. PATENT DOCUMENTS

2004/0067575 A1*  4/2004  Hanaoka ......... G01N 33/56905
                                                              435/252.3
2006/0223137 A1* 10/2006  Yoshida .......... G01N 33/56905
                                                              435/34
(Continued)

FOREIGN PATENT DOCUMENTS

CN        101846671 A      9/2010
CN        104965068 A     10/2015
(Continued)

OTHER PUBLICATIONS

Xiahui Ouyang et al., "Experimental Instruction on Basic Biology", p. 81-p. 85, Gansu Science and Technology Press, Jun. 1, 2015, with partial English translation of p. 83-p. 84.
(Continued)

*Primary Examiner* — Michael P LaPage
(74) *Attorney, Agent, or Firm* — Brinks Gilson & Lione

(57) ABSTRACT

Disclosed is a blood analyzer that includes: a sample preparation unit configured to mix a blood specimen and a fluorescent dye for staining nucleic acid to prepare a measurement sample; a light receiver configured to receive fluorescence and scattered light that are generated by light being applied to the measurement sample prepared by the sample preparation unit; and a controller programmed to determine whether or not infection with Plasmodium has occurred, on the basis of a value representing variation of a distribution of first particles in a range where single-ring form of red blood cells appear, the range where single-ring form of red blood cells appear being identified according to fluorescence intensities and scattered light intensities obtained by processing of signals from the light receiver.

16 Claims, 23 Drawing Sheets

(51) Int. Cl.
*G01N 15/14* (2006.01)
*G01N 33/569* (2006.01)
*G01N 1/30* (2006.01)
*G01N 21/64* (2006.01)
*G01N 15/10* (2006.01)
*G01N 15/00* (2006.01)

(52) U.S. Cl.
CPC ..... *G01N 15/1456* (2013.01); *G01N 15/1459* (2013.01); *G01N 21/6428* (2013.01); *G01N 33/56905* (2013.01); *G01N 2015/0073* (2013.01); *G01N 2015/1006* (2013.01); *G01N 2015/1402* (2013.01); *G01N 2015/1497* (2013.01); *G01N 2021/6439* (2013.01); *G01N 2333/445* (2013.01); *Y02A 50/30* (2018.01)

(58) Field of Classification Search
CPC ........... G01N 2021/4766; G01N 33/80; G01N 15/1429; G01N 33/56905; G01N 15/1456; G01N 15/1459; G01N 1/30; G01N 2015/1006; G01N 2015/1497; G01N 2333/445; G01N 2015/1402; G01N 2015/0073; G01N 2021/6439; G01N 21/47; G01N 21/6486; C12Q 1/06; Y02A 50/30
See application file for complete search history.

(56) References Cited

U.S. PATENT DOCUMENTS

| | | |
|---|---|---|
| 2010/0248300 A1 | 9/2010 | Yoshida et al. |
| 2014/0308697 A1* | 10/2014 | Ye .................... G01N 21/51 435/34 |
| 2015/0369793 A1 | 12/2015 | Kimura et al. |
| 2016/0061732 A1 | 3/2016 | Yamada et al. |
| 2017/0059486 A1 | 3/2017 | Suzuki et al. |

FOREIGN PATENT DOCUMENTS

| | | |
|---|---|---|
| CN | 105277519 A | 1/2016 |
| CN | 105388100 A | 3/2016 |
| CN | 105699277 A | 6/2016 |
| CN | 106483109 A | 3/2017 |
| JP | 2004-105027 A | 4/2004 |
| JP | 2006-304774 A | 11/2006 |

OTHER PUBLICATIONS

The Chinese Office Action dated Sep. 27, 2020 in a counterpart Chinese patent application No. 201710602108.1.
Japanese Office Action dated Feb. 9, 2021 in a counterpart Japanese patent application No. 2017-118936.
Japanese Office Action dated Mar. 9, 2021 in a counterpart Japanese patent application No. 2017-118936.

* cited by examiner

FIG. 1
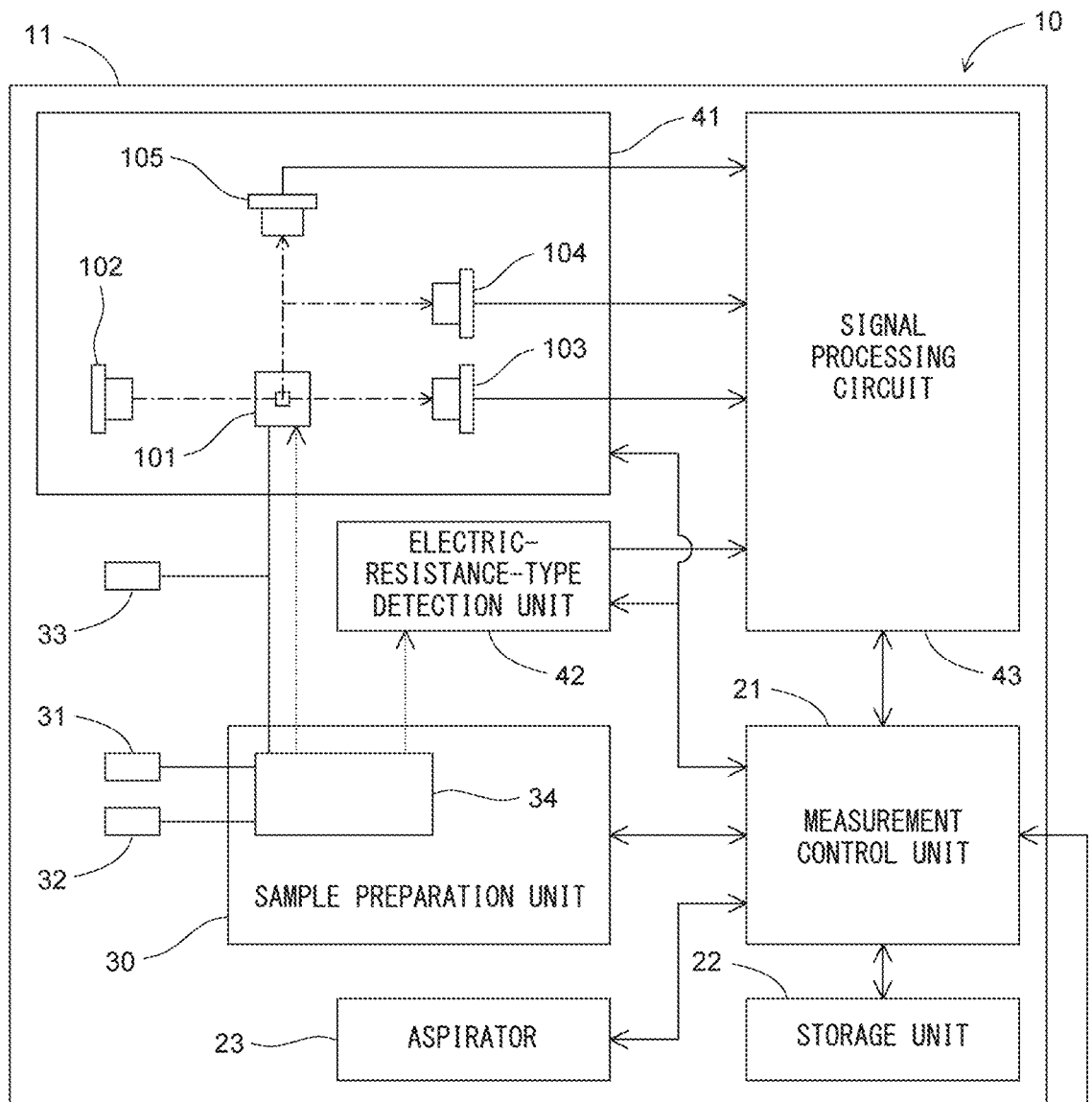
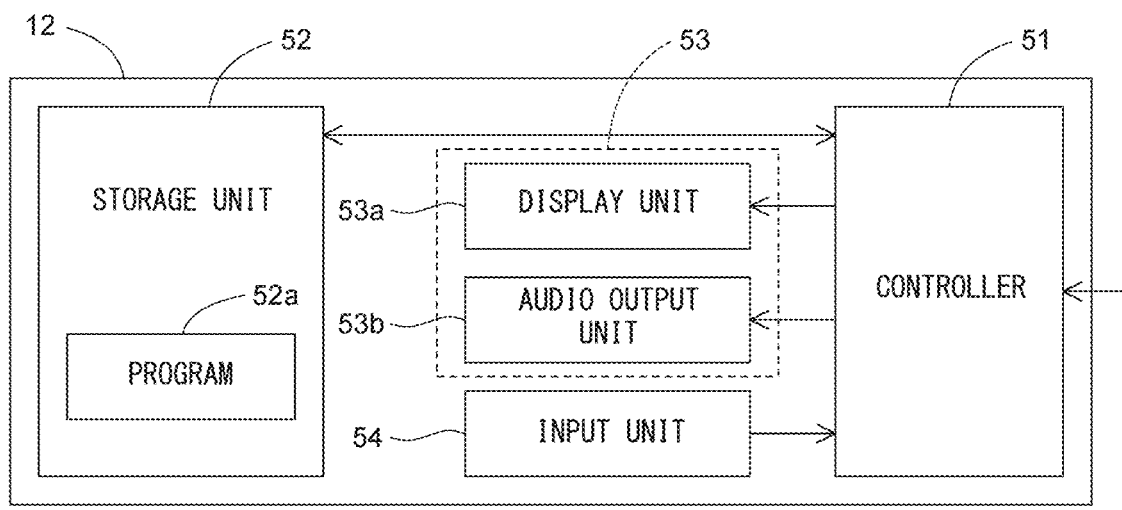

FIG. 11A  VERIFICATION EXAMPLE 1 (STEP S111 + STEP S116)

|  | DETERMINED AS POSITIVE | DETERMINED AS NEGATIVE | TOTAL |
|---|---|---|---|
| POSITIVE SPECIMEN | 27 | 0 | 27 |
| NEGATIVE SPECIMEN | 2 | 128 | 130 |

| SENSITIVITY | 27/27=100% |
|---|---|
| SPECIFICITY | 128/130≈98.5% |

FIG. 11B  VERIFICATION EXAMPLE 2 (ONLY STEP S111)

|  | DETERMINED AS POSITIVE | DETERMINED AS NEGATIVE | TOTAL |
|---|---|---|---|
| POSITIVE SPECIMEN | 27 | 0 | 27 |
| NEGATIVE SPECIMEN | 82 | 48 | 130 |

| SENSITIVITY | 27/27=100% |
|---|---|
| SPECIFICITY | 48/130≈36.9% |

FIG. 14A  BEFORE APOPTOSIS IS INDUCED
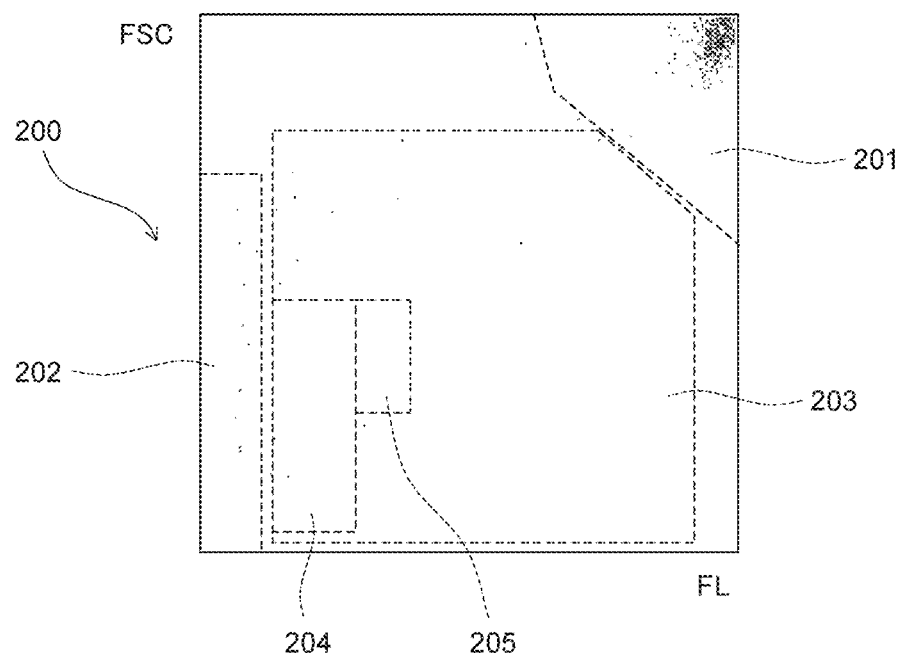
FIG. 14B  AFTER APOPTOSIS HAS BEEN INDUCED
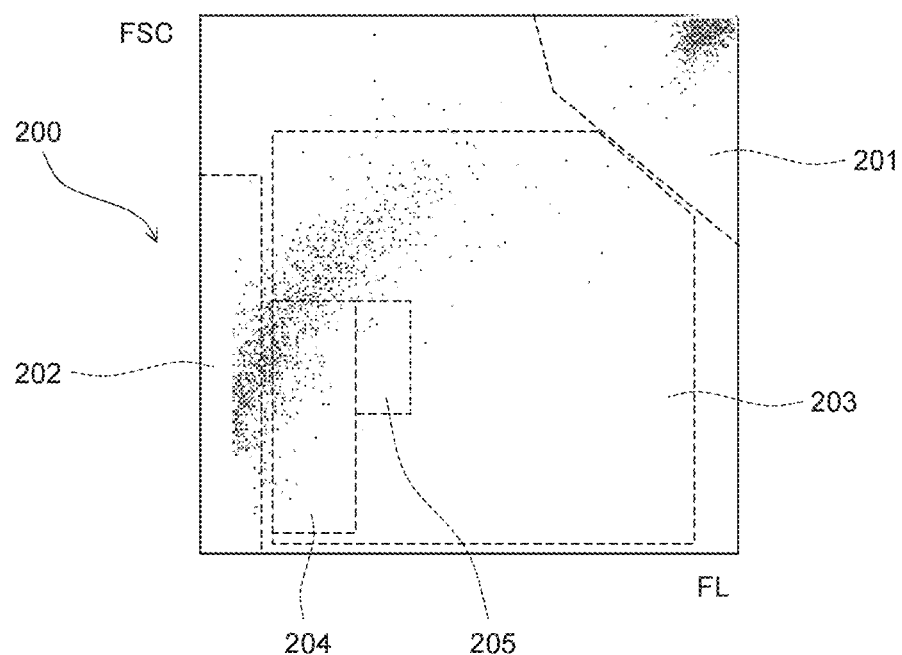

BLOOD ANALYZER AND BLOOD ANALYZING METHOD FOR DETERMINING IF PLASMODIUM INFECTION IS PRESENT

RELATED APPLICATIONS

This application is a continuation of application Ser. No. 15/657,962, filed Jul. 24, 2017, which claims priority from prior Japanese Patent Application Nos. 2016-145834, filed on Jul. 25, 2016, and 2017-118936, filed on Jun. 16, 2017, each entitled "Blood Analyzer and Blood Analyzing Method", the entire contents of each of which are incorporated herein by reference.

BACKGROUND OF THE INVENTION

1. Field of the Invention

The present invention relates to a blood analyzer and a blood analyzing method.

2. Description of the Related Art

A method for detecting a red blood cell infected with Plasmodium by flow cytometry is known. As shown in FIG. 23, Japanese Laid-Open Patent Publication No. 2006-304774 indicates that, in a scattergram having two axes of a scattered light intensity (FSCL) and a fluorescence intensity (SFLL), red blood cells infected with Plasmodium appear in a range where fluorescence intensities are higher than those of red blood cells which are not infected with malaria, and lower than those of white blood cells. In the scattergram, red blood cells including Plasmodium at predetermined stages in the life cycle, for example, red blood cells infected with ring form (single) Plasmodium, red blood cells infected with ring form (multi) Plasmodium, red blood cells infected with trophozoites of Plasmodium, and red blood cells infected with schizonts of Plasmodium appear in different regions in order, respectively, from a region where the fluorescence intensity is low. An infection rate and the like are determined for red blood cells infected with Plasmodium on the basis of malaria-infected red blood cells which have been thus detected.

The inventors have found that, in a case where whether or not infection with Plasmodium has occurred is determined on the basis of a particle distribution in such a scattergram, the malaria determination result is positive although a subject does not suffer from malaria, that is, so-called false-positive occurs, in some cases.

SUMMARY OF THE INVENTION

The scope of the present invention is defined solely by the appended claims, and is not affected to any degree by the statements within this summary.

A first mode of the present invention is a blood analyzer. The blood analyzer (10) according to this mode includes: a sample preparation unit (30) configured to mix a blood specimen and a fluorescent dye for staining nucleic acid to prepare a measurement sample; a light receiver (103, 105) configured to receive fluorescence and scattered light that are generated by light being applied to the measurement sample prepared by the sample preparation unit (30); and a controller (51) programmed to determine whether or not infection with Plasmodium has occurred, on the basis of a value representing variation of a distribution of first particles (G4) in a range (204) where single-ring form of red blood cells appear, the range of single-ring form of red blood cells appear being identified according to fluorescence intensities and scattered light intensities obtained by processing of signals from the light receiver (103, 105).

In the blood analyzer according to this mode, the single-ring form of red blood cell represents a red blood cell that includes one ring-form Plasmodium. The range where the single-ring form of red blood cells appear represents, for example, a region where the single-ring form of red blood cells are generally distributed when a scattergram is generated on the basis of fluorescence intensities and scattered light intensities. The first particles are a group of particles classified as the single-ring form of red blood cells. The value representing variation of a distribution of the first particles indicates a variation degree to which the particles in the first particles are distributed in the range where the single-ring form of red blood cells appear. The value representing variation of a distribution of the first particles is, for example, a value indicating variation of the frequency distribution with respect to fluorescence intensities of the first particles. The value representing variation of the frequency distribution is a value associated with variation of frequency, in the frequency distribution, with which particles appear, and is, for example, a coefficient of variation, a standard deviation, a half-value width in a frequency distribution chart, or the like. "Determine whether or not infection with Plasmodium has occurred" conceptually indicates not only that whether or not a red blood cell infected with Plasmodium is present is strictly determined, but also that whether or not a certain number of red blood cells infected with Plasmodium are in a blood specimen is determined.

A second mode of the present invention is a blood analyzing method. The blood analyzing method according to this mode includes determining (S103, S111 to S118, S121 to S128) whether or not infection with Plasmodium has occurred, on the basis of a value representing variation of a distribution of first particles (G4) in a range (204) where single-ring form of red blood cells appear, the range of single-ring form of red blood cells appear being identified according to fluorescence and scattered light generated by light being applied to a measurement sample, the measurement sample being prepared by mixing a blood specimen and a fluorescent dye for staining nucleic acid.

A third mode of the present invention is a blood analyzer. The blood analyzer (10) according to this mode includes: a sample preparation unit (30) configured to mix a blood specimen and a fluorescent dye for staining nucleic acid to prepare a measurement sample; and a light receiver (105) configured to receive fluorescence generated by light being applied to the measurement sample prepared by the sample preparation unit (30); and a controller (51) programmed to determine whether at least one of a red blood cell including an inclusion body of nucleic acid, and an extracellular vesicle is present or absent, on the basis of fluorescence intensities obtained by processing of signals from the light receiver (105).

The extracellular vesicle is a vesicle that is released from a cell, and conceptually includes a fine particle derived from a nucleated cell and a fine particle derived from a non-nucleated cell. Examples of the extracellular vesicle include exosomes, microvesicles (MV), apoptotic bodies, and the like.

The red blood cell including an inclusion body of nucleic acid is a red blood cell including an inclusion body, of nucleic acid, which is left after nucleic acid has been agglutinated inside a cell. Examples of the inclusion body of nucleic acid include a Howell-Jolly body and basophilic stippling. As to a reticulocyte, RNAs thereinside are dispersed in the reticulocyte, and nucleic acid does not exist in an agglutinated form. Therefore, the reticulocyte is different from a red blood cell including an inclusion body of nucleic acid.

"Determine whether at least one of: a red blood cell including an inclusion body of nucleic acid; and an extracellular vesicle is present or absent" conceptually means whether or not at least one of a red blood cell including an inclusion body of nucleic acid; and an extracellular vesicle is present is determined, whether an extracellular vesicle is present or absent is determined, and whether a blood cell including an inclusion body of nucleic acid is present or absent is determined. In a case where whether or not at least one of a red blood cell including an inclusion body of nucleic acid; and an extracellular vesicle is present is determined, the determination result indicates that, for example, "at least one of them is present" or "both of them are not present". In a case where whether an extracellular vesicle is present or absent is determined, the determination result indicates that, for example, "an extracellular vesicle is present" or "an extracellular vesicle is absent". In a case where whether a red blood cell including an inclusion body of nucleic acid is present or absent is determined, the determination result indicates that, for example, "a red blood cell including an inclusion body of nucleic acid is present" or "a red blood cell including an inclusion body of nucleic acid is absent". "Whether a particle is present or absent is determined" conceptually indicates not only that whether or not the particle is present is strictly determined, but also that whether or not a predetermined amount of the particles are present in a blood specimen is determined.

A fourth mode of the present invention is a blood analyzing method. The blood analyzing method according to this mode includes determining (S103, S121 to S128, S131 to S136) whether at least one of a red blood cell including an inclusion body of nucleic acid, and an extracellular vesicle is present or absent, on the basis of fluorescence generated by light being applied to a measurement sample prepared by mixing a blood specimen, and a fluorescent dye for staining nucleic acid.

BRIEF DESCRIPTION OF THE DRAWINGS

FIG. 1 is a block diagram illustrating a configuration of a blood analyzer according to Embodiment 1;

FIG. 11A illustrates a result of verification of a determination process performed by the inventors, according to Embodiment 1;

FIG. 11B illustrates a result of verification of a determination process performed by the inventors, according to Embodiment 1;

FIG. 14A illustrates a scattergram generated based on Jurkat cells to which apoptosis has not been induced yet, according to Embodiment 1;

FIG. 14B illustrates a scattergram generated based on the Jurkat cells after apoptosis has been induced, according to Embodiment 1;

DETAILED DESCRIPTION OF THE PREFERRED EMBODIMENTS

Embodiment 1

Figure 2:
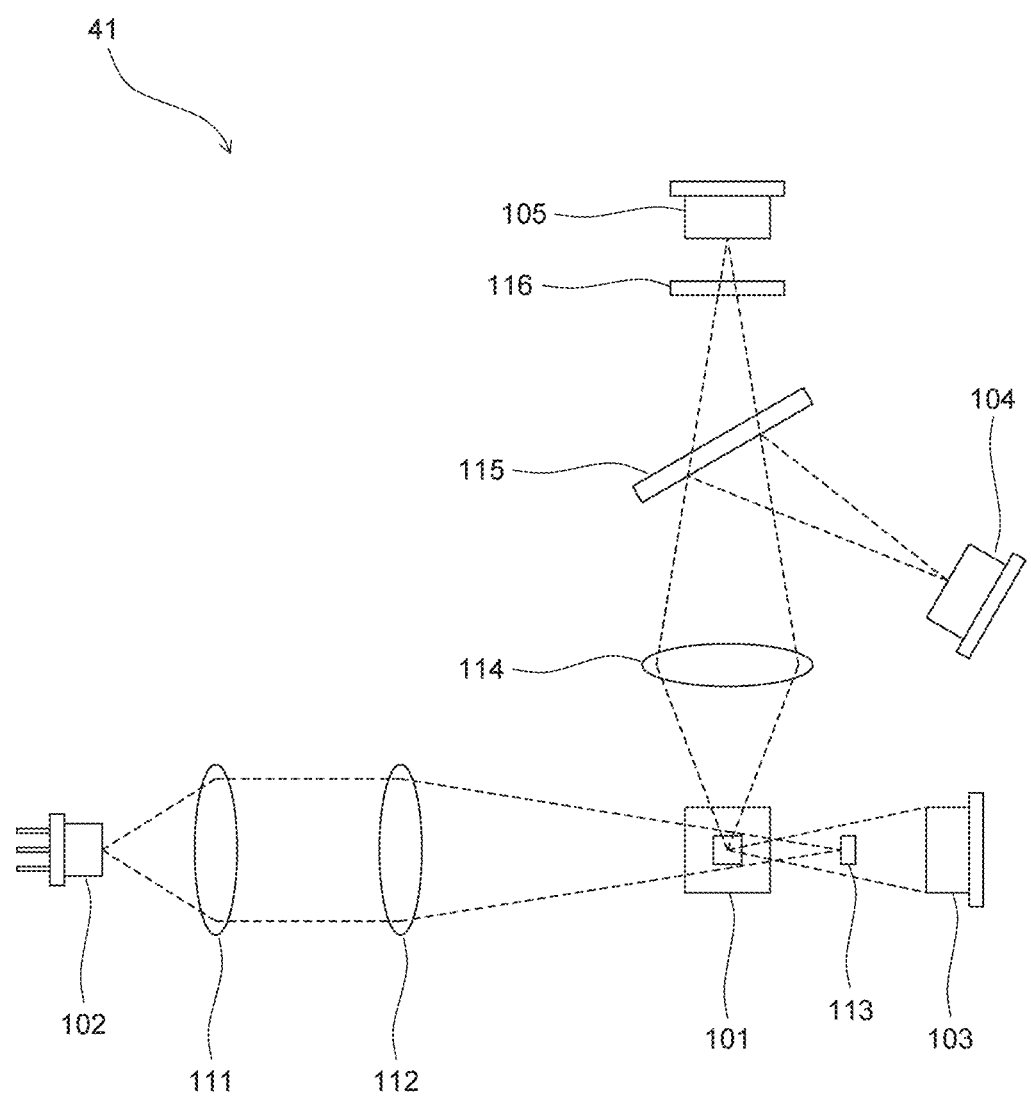
FIG. 2 is a schematic diagram illustrating a structure of an optical detection unit according to Embodiment 1.

A blood analyzer 10 according to Embodiment 1 measures a measurement sample prepared from a blood specimen and a reagent, identifies a group that includes red blood cells infected with Plasmodium, and determines whether or not the blood specimen is infected with malaria.

When a merozoite that is one of forms of Plasmodium enters a red blood cell, an erythrocytic life cycle of the Plasmodium starts. In the erythrocytic life cycle, the form of the Plasmodium changes to ring form, trophozoite, schizont, in order, respectively. The schizont divides into a plurality of merozoites. At this time, the red blood cell is destroyed. Thus, multiple merozoites are released into the blood. The merozoite enters another red blood cell, and the erythrocytic life cycle starts again. Such a cycle is repeated, and the Plasmodium proliferates. A part of the merozoites released into the blood differentiates into dioecious gametocytes. In a case where an infected person is blood-sucked by a mosquito, the gametocytes enter the body of the mosquito, and the mosquito has the Plasmodium.

Hereinafter, a red blood cell which is not infected with Plasmodium is referred to as "non-malaria-infected red blood cell". The non-malaria-infected red blood cells include reticulocytes as well as mature red blood cells. A red blood cell infected with Plasmodium is referred to as "malaria-infected red blood cell". The malaria-infected red blood cells include a red blood cell infected with ring form Plasmodium, a red blood cell infected with trophozoite of Plasmodium, and a red blood cell infected with schizont of Plasmodium. A red blood cell infected with one ring-form Plasmodium, that is, a red blood cell including ring-form Plasmodium the number of which is one, is referred to as "single-ring form of red blood cell". A red blood cell infected with a plurality of ring-form Plasmodium, that is, a red blood cell including ring-form Plasmodium the number of which is plural, is referred to as "multi-ring form of red blood cell".

As shown in FIG. 1, the blood analyzer 10 includes a measurement unit 11 and an information processing unit 12. The measurement unit 11 includes a measurement control unit 21, a storage unit 22, an aspirator 23, a sample preparation unit 30, an optical detection unit 41, an electric-resistance-type detection unit 42, and a signal processing circuit 43.

The measurement control unit 21 includes, for example, a CPU and an MPU. The measurement control unit 21 receives signals outputted by components of the measurement unit 11, and controls the components of the measurement unit 11. The measurement control unit 21 performs communication with the information processing unit 12. The storage unit 22 includes, for example, a ROM, a RAM, and a hard disk. The measurement control unit 21 performs a process based on a program stored in the storage unit 22. The aspirator 23 has a not-illustrated aspiration tube, and aspirates a blood specimen contained in a not-illustrated specimen container by using the aspiration tube. The blood specimen is peripheral whole blood collected from a subject.

The specimen container is transported by a rack transporter in a state where the specimen container is held by a not-illustrated specimen rack, and is positioned at a removal position. The specimen container positioned at the removal position is taken out from the specimen rack to perform agitation. Thereafter, the specimen container is transported to an aspiration position at which the aspirator 23 performs aspiration. When the specimen container is positioned at the aspiration position, the aspirator 23 aspirates the blood specimen contained in the specimen container by using the aspiration tube. Thereafter, the specimen container is returned to the previous position in the specimen rack. In a case where the blood analyzer 10 does not have a structure for transporting a specimen rack and a structure for transporting a specimen container, an operator positions the specimen container at the aspiration position.

To the sample preparation unit 30, reagent containers 31, 32, 33 are connected. The reagent container 31 stores a first diluent that causes a red blood cell to contract. The reagent container 32 stores a staining reagent that includes a fluorescent dye that specifically stains nucleic acid. The reagent container 33 stores a second diluent. The sample preparation unit 30 has a reactor 34. The aspirator 23 allows the aspiration tube to move so as to be above the reactor 34, and discharges the aspirated blood specimen into the reactor 34. In the reactor 34, the blood specimen, the first diluent, and the staining reagent are mixed, to prepare a first measurement sample. The first measurement sample is used to measure a white blood cell and a malaria-infected red blood cell. In the reactor 34, the blood specimen and the second diluent are mixed to prepare a second measurement sample. The second measurement sample is used to measure a red blood cell and a platelet.

The first diluent, the second diluent, and the staining reagent will be described.

The first diluent includes two kinds of surfactants having different hemolyzing abilities. Specifically, the first diluent includes 2.95 mM of lauryl trimethyl ammonium chloride that is a cationic surfactant, and 1.11 mM of stearyl trimethyl ammonium chloride that is a cationic surfactant. Stearyl trimethyl ammonium chloride has a higher hemolyzing ability than lauryl trimethyl ammonium chloride. The two kinds of the surfactants may be another combination of surfactants in a case where the surfactants have different hemolyzing abilities.

The first diluent further includes 2.90 mM of PBC-44 which is a nonionic surfactant, 20 mM of ADA, an appropriate amount of NaCl, and 1 L of purified water. The pH of ADA is 6.1. The pH of the first diluent is greater than or equal to 5.0 and not greater than 7.0. In order to contract a blood cell, the osmotic pressure of the first diluent is preferably higher than or equal to 200 mOsm/kg·$H_2O$. Specifically, the osmotic pressure of the first diluent is higher than or equal to 200 mOsm/kg·$H_2O$ and not higher than 300 mOsm/kg·$H_2O$.

By the first diluent as described above, red blood cells are contracted, and a malaria-infected red blood cell is contracted in a state where the malaria-infected red blood cell has Plasmodium thereinside, by the first measurement sample being prepared. The first diluent allows the fluorescent dye to permeate through a red blood cell, and allows a cell membrane of the red blood cell to be lysed to such a degree as to maintain the shape of the red blood cell. In the case of a malaria-infected red blood cell, specifically, the cell membrane of the red blood cell is partially lysed such that the fluorescent dye permeates in a state where Plasmodium is held in the red blood cell.

The second diluent is a diluent for measuring a red blood cell by a sheath flow DC detection method, unlike the first diluent that causes a red blood cell to contract. The second diluent is used also as a sheath liquid for flowing the first measurement sample through a flow cell 101 of the optical detection unit 41, and a sheath liquid for flowing the second measurement sample through a flow cell of the electric-resistance-type detection unit 42. The first diluent is not used as a sheath liquid.

The staining reagent includes a fluorescent dye that specifically stains nucleic acid, and preferably includes a fluorescent dye that stains DNA more intensely than RNA. In Embodiment 1, the fluorescent dye is, for example, Hoechst 34580. The staining reagent is obtained by dissolving a fluorescent dye in a solvent, and the solvent for the staining reagent is, for example, ethylene glycol. The concentration of the fluorescent dye in the staining reagent is preferably greater than or equal to 0.3 µM and preferably not greater than 0.6 µM, and is specifically 0.45 µM. The concentration of the fluorescent dye in the first measurement sample is preferably greater than or equal to 0.15 µM and preferably not greater than 1.0 µM. The chemical formula of Hoechst 34580 is as follows.

[Chemical formula 1]

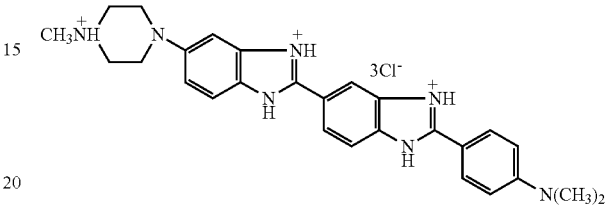

A non-malaria-infected red blood cell is rarely stained by the above-described fluorescent dye since the non-malaria-infected red blood cell has no nucleus. Meanwhile, in the case of a malaria-infected red blood cell, nucleic acid of Plasmodium that has entered the red blood cell is stained. Thus, a non-malaria-infected red blood cell is rarely stained by the fluorescent dye, while a malaria-infected red blood cell is stained by the fluorescent dye. Therefore, discrimination between a non-malaria-infected red blood cell and a malaria-infected red blood cell can be performed on the basis of a difference between fluorescence intensities in a scattergram described below. A white blood cell has a nucleus, and is thus stained by the fluorescent dye. The platelet aggregation has no nucleuses, and is rarely stained by the fluorescent dye.

One reagent that contains the first diluent and the fluorescent dye may be mixed with a blood specimen without separating the first diluent and the staining reagent from each other, to prepare the first measurement sample.

The optical detection unit 41 performs a first measurement, by flow cytometry, on the basis of the first measurement sample. The optical detection unit 41 includes the flow cell 101, a light source 102, and light receivers 103, 104, 105. In the first measurement, the first measurement sample is supplied into the flow cell 101 through a flow path from the sample preparation unit 30.

Light emitted from the light source 102 is applied to the first measurement sample that flows through the flow cell 101. When the light from the light source 102 is applied to the first measurement sample, forward scattered light, side scattered light, and fluorescence are generated from particles in the first measurement sample. The light receivers 103 to 105 receive the forward scattered light, the side scattered light, and the fluorescence, respectively. The light receivers 103 to 105 each output a signal based on the received light, to the signal processing circuit 43. The configuration of the optical detection unit 41 will be described below in detail with reference to FIG. 2.

The electric-resistance-type detection unit 42 performs a second measurement, by using a sheath flow DC detection method, on the basis of the second measurement sample. In the second measurement, the second measurement sample is supplied into a not-illustrated flow cell of the electric-resistance-type detection unit 42 through a flow path from the sample preparation unit 30. The electric-resistance-type detection unit 42 applies voltage to the second measurement sample that flows through the flow cell of the electric-resistance-type detection unit 42, and detects change of voltage due to passing of a particle, to detect the particle. The electric-resistance-type detection unit 42 outputs a detection signal to the signal processing circuit 43.

The signal processing circuit 43 performs signal processing of the signals outputted from the light receivers 103 to 105. Specifically, the signal processing circuit 43 extracts a waveform corresponding to the particle on the basis of the signal outputted from each of the light receivers 103 to 105, and calculates, as first information, a peak value, a width, an area, and the like of the waveform for each particle. Hereinafter, the peak values of the waveforms based on the signals outputted from the light receivers 103 and 105 are referred to as "forward scattered light intensity" and "fluorescence intensity", respectively. Each of the forward scattered light intensity and the fluorescence intensity may represent a width or an area of the waveform. The signal processing circuit 43 calculates, as second information, the peak value of the signal outputted from the electric-resistance-type detection unit 42.

The measurement control unit 21 causes the storage unit 22 to store the first information obtained by the signal processing circuit 43 performing the signal processing in the first measurement, and the second information obtained by the signal processing circuit 43 performing the signal processing in the second measurement. When the first measurement and the second measurement are ended, the measurement control unit 21 transmits, as measurement data, the first information and the second information stored in the storage unit 22, to the information processing unit 12.

The information processing unit 12 includes a controller 51, a storage unit 52, an output unit 53, and an input unit 54. The output unit 53 includes a display unit 53a and an audio output unit 53b.

The controller 51 includes, for example, a CPU and an MPU. The controller 51 receives signals outputted from components of the information processing unit 12, and controls the components of the information processing unit 12. The controller 51 performs communication with the measurement unit 11. The storage unit 52 includes, for example, a ROM, a RAM, and a hard disk. The controller 51 performs a process based on a program 52a stored in the storage unit 52. The program 52a includes a program for performing processes described below with reference to FIG. 4, FIG. 5A, and FIG. 6.

The controller 51 determines whether or not infection with Plasmodium has occurred, on the basis of a value representing variation of a distribution of particles in a range where single-ring form of red blood cells identified on the basis of fluorescence intensities and scattered light intensities appear. Thus, whether or not a malaria-infected red blood cell is included in the particles in the range where the single-ring form of red blood cells appear, can be clearly determined. Therefore, so-called false-positive which indicates that malaria determination result is positive although a subject is not infected with malaria, can be inhibited from occurring. Therefore, whether or not infection with Plasmodium has occurred can be determined with enhanced accuracy. The determination process by the controller 51 will be described below with reference to FIG. 6.

The display unit 53a displays information. The display unit 53a is implemented as, for example, a display. The audio output unit 53b outputs information as an audio. The audio output unit 53b is implemented as, for example, a speaker. The input unit 54 includes a mouse or a keyboard.

The controller 51 causes the storage unit 52 to store analysis result and the like, and causes the analysis result and the like to be outputted to the output unit 53. The controller 51 receives an instruction from an operator through the input unit 54.

Next, the optical detection unit 41 shown in FIG. 1 will be described in detail.

As shown in FIG. 2, the optical detection unit 41 includes the flow cell 101, the light source 102, the light receivers 103 to 105, a collimator lens 111, a condenser lens 112, a beam stopper 113, a condenser lens 114, a dichroic mirror 115, and an optical filter 116.

The flow cell 101 is formed from a translucent material into a tubular shape. The first measurement sample flows through the flow cell 101 in a state where the first measurement sample is surrounded by a sheath liquid. Thus, particles contained in the first measurement sample flow through the flow cell 101 in a state where the particles are aligned in line.

The light source 102 emits light in a blue-violet wavelength band. Specifically, the light source 102 is a semiconductor laser light source, and emits blue-violet laser light having a wavelength of 405 nm. By the light emitted from the light source 102, the fluorescent dye included in the staining reagent is excited, and fluorescence in a predetermined wavelength band is generated from the fluorescent dye. The light source 102 may emit light in a band other than the blue-violet wavelength band in a case where fluorescence can be generated from the fluorescent dye by the emitted light. In a case where the wavelength of light emitted from the light source 102 is shorter, light applied to the flow cell 101 can be converged so as to be small, whereby detection for a smaller particle can be performed. Therefore, the wavelength of light emitted from the light source 102 is advantageously set so as to be in the blue-violet wavelength band described above.

The light emitted from the light source 102 is condensed by the collimator lens 111 and the condenser lens 112, and applied to the first measurement sample that flows through the flow cell 101. As described above, when light is applied to the first measurement sample, forward scattered light, side scattered light, and fluorescence are generated from the particle in the first measurement sample. The forward scattered light represents the information about the size of the particle, the side scattered light represents the information about the inside of the particle, and the fluorescence represents the degree of staining of the particle. Light, among light applied to the flow cell 101, which has not been applied to the particle and has transmitted through the flow cell 101 is blocked by the beam stopper 113. The light receiver 103 is implemented as, for example, a photodiode. The light receiver 103 receives the forward scattered light and outputs an electrical signal according to the received forward scattered light.

The fluorescence and the side scattered light generated in the lateral direction of the flow cell 101 are condensed by the condenser lens 114. The dichroic mirror 115 reflects the side scattered light that is condensed by the condenser lens 114, and allows the fluorescence condensed by the condenser lens 114 to transmit therethrough. The light receiver 104 is implemented as, for example, a photodiode. The light receiver 104 receives the side scattered light reflected by the dichroic mirror 115, and outputs an electrical signal according to the received side scattered light. The optical filter 116 allows only the fluorescence to be received by the light receiver 105, among the light that has transmitted through the dichroic mirror 115, to transmit therethrough. The light receiver 105 is implemented as, for example, an avalanche photodiode. The light receiver 105 receives the fluorescence that has transmitted through the optical filter 116, and outputs an electrical signal according to the received fluorescence.

Next, the process performed by the measurement unit 11 will be described with reference to a flow chart.

Figure 3:
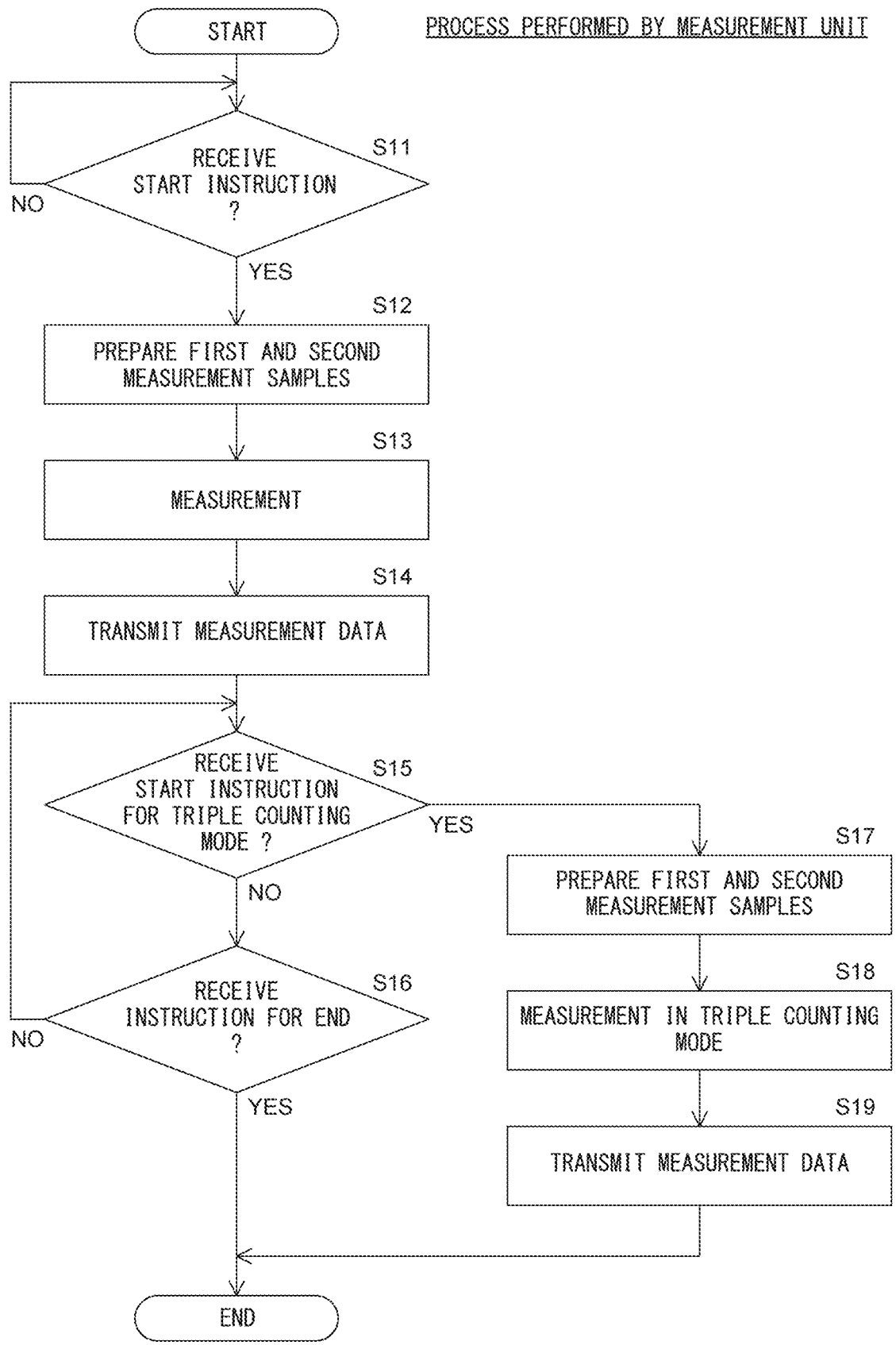
FIG. 3 is a flow chart showing a process performed by a measurement unit according to Embodiment 1.

As shown in FIG. 3, in step S11, the measurement control unit 21 determines whether or not a start instruction has been received from the information processing unit 12. When the start instruction has been received, the measurement control unit 21 causes the first measurement sample and the second measurement sample to be prepared in step S12.

Specifically, the specimen rack is transported by the rack transporter, and the specimen container is positioned at a removal position. The measurement control unit 21 controls the components of the measurement unit 11 such that the specimen container is taken out from the specimen rack at the removal position to perform agitation, and the specimen container is positioned at the aspiration position after the agitation. The measurement control unit 21 controls the aspirator 23 such that the blood specimen is aspirated from the specimen container by using the aspiration tube, and the aspirated blood specimen is discharged into the reactor 34. The specimen container from which the blood specimen has been aspirated, is returned to the previous position of the specimen rack. The measurement control unit 21 controls the sample preparation unit 30 such that the blood specimen, the first diluent, and the staining reagent are mixed in the reactor 34, to prepare the first measurement sample. The measurement control unit 21 controls the sample preparation unit 30 such that the blood specimen and the second diluent are mixed in the reactor 34 to prepare the second measurement sample.

In a case where the blood analyzer 10 does not have a structure for transporting the specimen rack and a structure for transporting the specimen container, the measurement control unit 21 controls the aspirator 23 such that the blood specimen is aspirated by using the aspiration tube from the specimen container positioned at the aspiration position by an operator.

In step S13, the measurement control unit 21 controls the optical detection unit 41 so as to perform the first measurement, and controls the electric-resistance-type detection unit 42 so as to perform the second measurement. At this time, the measurement control unit 21 causes the first measurement sample to flow through the flow cell 101, and causes the storage unit 22 to store the first information obtained during a time T1. The measurement control unit 21 causes the second measurement sample to flow through the flow cell of the electric-resistance-type detection unit 42, and causes the storage unit 22 to store the second information obtained during a time T2. In step S14, the measurement control unit 21 transmits the first information and the second information which are stored in the storage unit 22 in the measurement of step S13, as measurement data in a normal mode, to the information processing unit 12.

Subsequently, in step S15, the measurement control unit 21 determines whether or not a start instruction for a triple counting mode has been received from the information processing unit 12. When the start instruction for the triple counting mode has not been received, the measurement control unit 21 determines, in step S16, whether or not an instruction for end has been received from the information processing unit 12. When the instruction for end has not been received, the process is returned to step S15. When the instruction for end is received without receiving the start instruction for the triple counting mode, the process performed by the measurement unit 11 is ended.

When the start instruction for the triple counting mode is received, the measurement control unit 21 causes the first measurement sample and the second measurement sample to be prepared again in step S17, as in step S12. In step S18, the measurement control unit 21 controls the optical detection unit 41 so as to perform the first measurement in the triple counting mode, and controls the electric-resistance-type detection unit 42 so as to perform the second measurement in the triple counting mode. At this time, the measurement control unit 21 causes the first measurement sample to flow through the flow cell 101, and causes the storage unit 22 to store the first information obtained during a time which is three times the time T1. The measurement control unit 21 causes the second measurement sample to flow through the flow cell of the electric-resistance-type detection unit 42, and cause the storage unit 22 to store the second information obtained during a time which is three times the time T2. Thus, the first information based on the first measurement sample of which the amount is about three times an amount in a normal mode measurement in step S13, and the second information based on the second measurement sample of which the amount is about three times an amount in the normal mode measurement in the step S13, are obtained.

In step S19, the measurement control unit 21 transmits the first information and the second information which are stored in the storage unit 22 in the measurement of step S18, as measurement data in the triple counting mode, to the information processing unit 12. Thus, the process performed by the measurement unit 11 is ended. When the process shown in FIG. 3 has been ended, the measurement control unit 21 returns the process to step S11, and causes the same measurement to be performed also for a subsequent blood specimen.

Next, the process performed by the information processing unit 12 will be described with reference to a flow chart.

Figure 4:
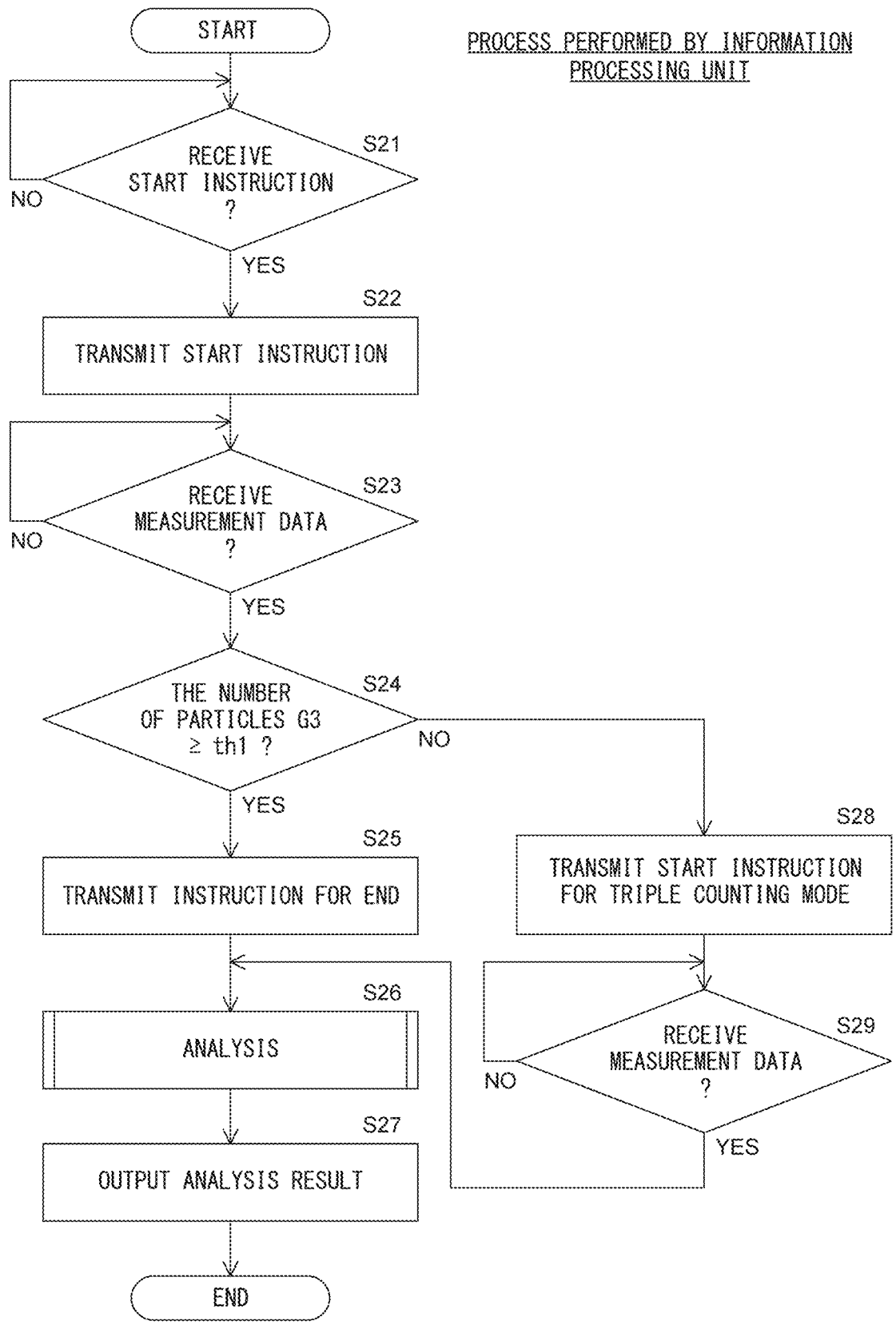
FIG. 4 is a flow chart showing a process performed by an information processing unit according to Embodiment 1.

As shown in FIG. 4, in step S21, the controller 51 determines whether or not a start instruction has been received from an operator through the input unit 54. When the start instruction is received from the operator, the controller 51 transmits the start instruction to the measurement unit 11 in step S22. Thus, in the measurement unit 11, step S12 and the subsequent process steps shown in FIG. 3 are started. Subsequently, in step S23, the controller 51 determines whether or not measurement data, in the normal mode, transmitted by the measurement unit 11 in step S14 shown in FIG. 3 has been received.

When the measurement data in the normal mode is received, the controller 51 determines, in step S24, whether or not the number of particles G3 per unit volume is greater than or equal to a threshold value th1, on the basis of the measurement data in the normal mode. The particles G3 represent particles included in a range where malaria-infected red blood cells appear as described below. The particles G3 will be described below with reference to FIG. 5B. The threshold value th1 is set to be greater than or equal to 100 and not greater than 500, and is set to, for example, 100. The threshold value th1 can be changed through the input unit 54 by an operator. In step S24, the controller 51 may determine whether or not the number of the particles G3 is greater than or equal to a predetermined threshold value.

In a case where the number of the particles G3 per unit volume is greater than or equal to the threshold value th1, the controller 51 transmits an instruction for end to the measurement unit 11 in step S25, and advances the process to step S26. Thus, the determination of step S16 shown in FIG.

3 is YES, and the process, performed by the measurement unit 11, shown in FIG. 3 is ended. Meanwhile, in a case where the number of the particles G3 per unit volume is less than the threshold value th1, the controller 51 transmits a start instruction for the triple counting mode to the measurement unit 11 in step S28. Thus, the determination of step S15 shown in FIG. 3 is YES, and the process steps of steps S17 to S19 shown in FIG. 3 are performed. Subsequently, in step S29, the controller 51 determines whether or not measurement data, in the triple counting mode, transmitted by the measurement unit 11 in step S19 shown in FIG. 3 has been received. When the measurement data in the triple counting mode has been received, the controller 51 advances the process to step S26.

In a case where the number of the particles G3 per unit volume is less than the threshold value th1, it is not preferable that, for example, "malaria-negative" is easily determined, in the determination process described below, on the basis of the measurement data in the normal mode. In some cases, even when a subject suffers from malaria, the number of the malaria-infected red blood cells in the blood specimen of the subject is small. In this case, when the determination is "malaria-negative", false-negative may occur. Also in a case where the number of malaria-infected red blood cells is gradually reduced by treatment, it is important to perform monitoring until the malaria-infected red blood cells completely disappear.

Therefore, in a case where the number of the particles G3 is small, the controller 51 further obtains the measurement data in the triple counting mode, and performs analysis described below by using the obtained measurement data in the triple counting mode. Thus, the analysis is performed by using the first information and the second information based on the number of blood cells which is about three times the number of blood cells obtained in the normal mode. Therefore, the obtained analysis result is less likely to depend on variation of the measurement sample and the like, and appropriately represents the state of the blood specimen. Therefore, a malaria analysis result can be prevented from being outputted with low accuracy.

Subsequently, in step S26, the controller 51 performs analysis. The analysis will be described below with reference to FIG. 5A. In step S27, the controller 51 outputs, to the output unit 53, the analysis result obtained in the analysis in step S26. Specifically, the controller 51 causes the display unit 53a to display, for example, information representing the number of the blood cells, a scattergram, a frequency distribution chart, determination result, and reliability, as the analysis result. The screen displayed on the display unit 53a will be described below with reference to FIG. 10. The controller 51 may output the information to a device other than the blood analyzer 10. The controller 51 may cause the audio output unit 53b to output, by audio, the number of the blood cells, the determination result, and the like.

When the process shown in FIG. 4 has been ended, the controller 51 returns the process to step S21. When a subsequent specimen container is present, the determination of step S21 is YES, and step S22 and the subsequent process steps are similarly performed for the subsequent blood specimen. When no subsequent specimen container is present, the controller 51 puts the process in a stand-by state in step S21 until a start instruction is received again.

Next, the analysis will be described with reference to a flow chart shown in FIG. 5A.

In steps S101, S102 described below, when measurement data in the triple counting mode is not received, the controller 51 performs counting by using the measurement data in the normal mode, and, when measurement data in the triple counting mode is received, the controller 51 performs counting by using the measurement data in the triple counting mode.

Figure 5A:
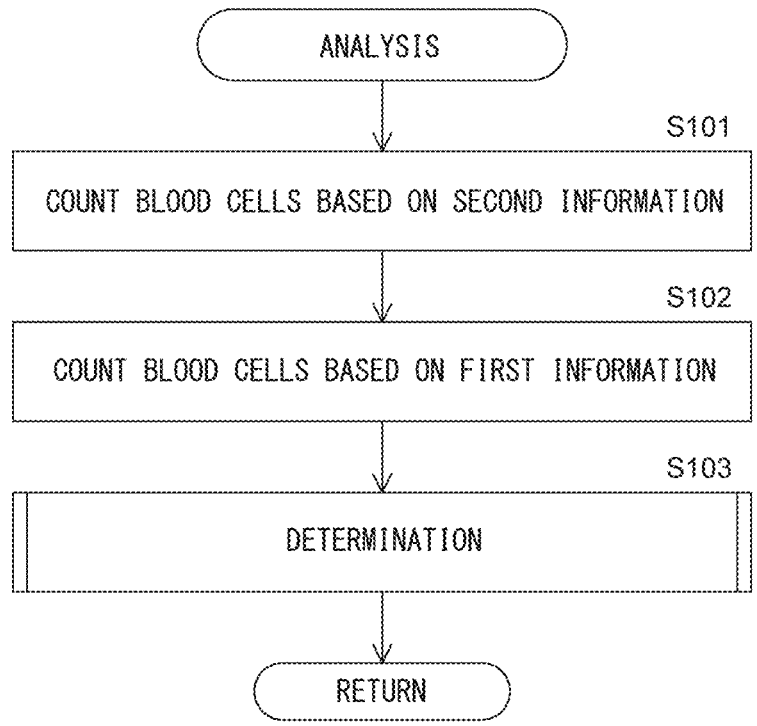
FIG. 5A is a flow chart showing an analysis according to Embodiment 1.

As shown in FIG. 5A, in step S101, the controller 51 counts blood cells on the basis of the second information included in the measurement data, that is, the second information obtained in the second measurement by the electric-resistance-type detection unit 42. Specifically, the controller 51 counts red blood cells and platelets. In step S102, the controller 51 counts blood cells on the basis of the first information included in the measurement data, that is, the first information obtained in the first measurement by the optical detection unit 41. Specifically, the controller 51 counts white blood cells, non-malaria-infected red blood cells, malaria-infected red blood cells, the single-ring form of red blood cells, and the multi-ring form of red blood cells.

Counting of the blood cells in step S102 will be described with reference to FIG. 5B.

Figure 5B:
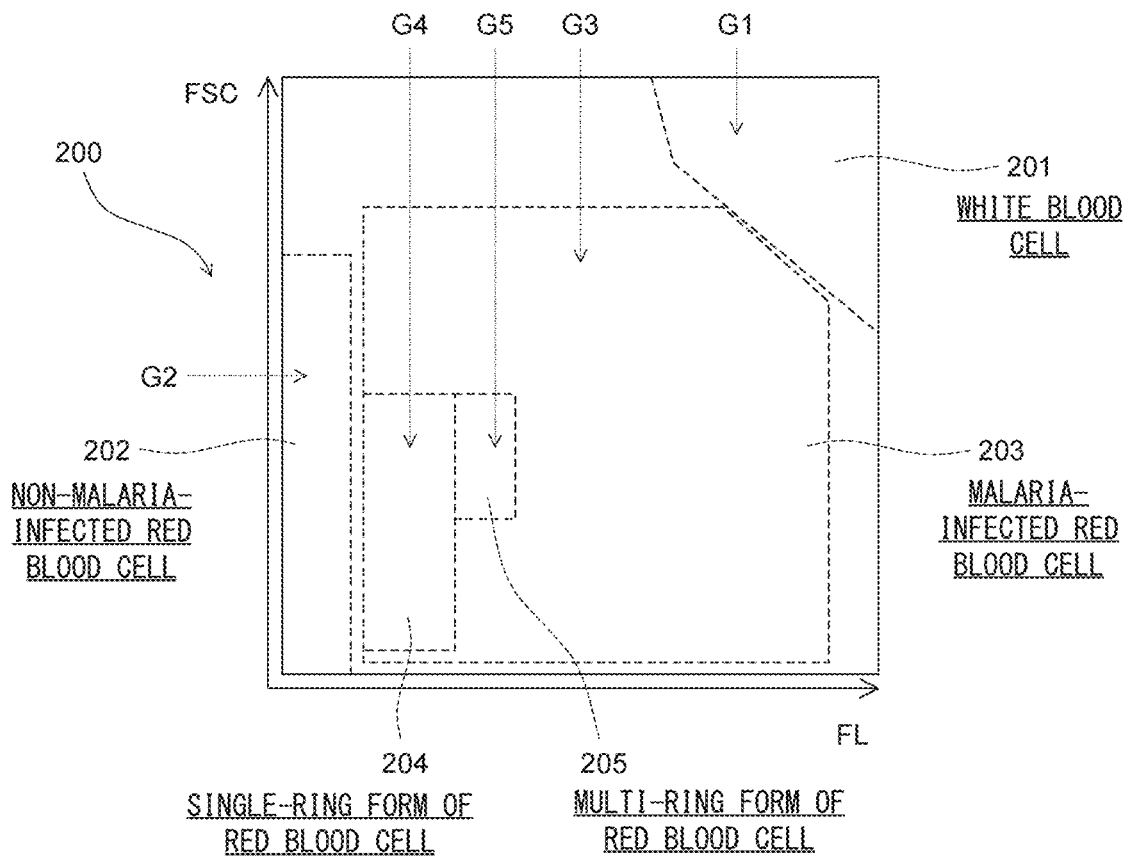
FIG. 5B is a schematic diagram illustrating a scattergram based on a first measurement according to Embodiment 1.

In a scattergram 200 shown in FIG. 5B, the vertical axis represents a forward scattered light intensity, and the horizontal axis represents a fluorescence intensity. The particles detected in the first measurement are plotted in the scattergram 200 on the basis of the forward scattered light intensity and the fluorescence intensity corresponding to each particle.

In the scattergram 200, the white blood cells are generally distributed in a region 201 where the forward scattered light intensity and the fluorescence intensity are high. The non-malaria-infected red blood cells are smaller than the white blood cells and are contracted by the first diluent. The non-malaria-infected red blood cells are not substantially stained by the fluorescent dye. Therefore, the non-malaria-infected red blood cells are generally distributed in a region 202. The forward scattered light intensity in the region 202 is lower than that in the region 201 corresponding to the white blood cells. The fluorescence intensity in the region 202 is lower than that in the region 201.

The malaria-infected red blood cells are also smaller than the white blood cells, and are contracted by the first diluent. The malaria-infected red blood cells are stained by the fluorescent dye since Plasmodium is held thereinside. Therefore, the malaria-infected red blood cells are generally distributed in a region 203. The forward scattered light intensity in the region 203 is lower than that in the region 201 corresponding to the white blood cells. The fluorescence intensity in the region 203 is higher than that in the region 202 corresponding to the non-malaria-infected red blood cells and lower than that in the region 201 corresponding to the white blood cells.

The malaria-infected red blood cell is contracted in a state where Plasmodium is held thereinside. Therefore, the malaria-infected red blood cell has the size corresponding to the form of Plasmodium held thereinside. Therefore, the single-ring form of red blood cell and the multi-ring form of red blood cell each have the size that is generally smaller than the size of the red blood cell that is infected with another form of Plasmodium, and the size of the single-ring form of red blood cell and the size of the multi-ring form of red blood cell are almost the same. The multi-ring form of red blood cell holds a plurality of Plasmodium thereinside, and the fluorescence intensity of the multi-ring form of red blood cell is higher than that of the single-ring form of red blood cell. Therefore, the single-ring form of red blood cells are generally distributed in a region 204, and the multi-ring form of red blood cells are generally distributed in a region 205. The regions 204, 205 are included in the region 203 corresponding to the malaria-infected red blood cells. The regions 204, 205 do not overlap each other, are adjacent to each other in the horizontal axis direction, and are positioned at the left end in the region 203. The fluorescence intensity in the region 205 is higher than that in the region 204.

"A fluorescence intensity in a first region is higher than a fluorescence intensity in a second region" means that the maximum value and the minimum value of the fluorescence intensity in the first region are greater than the maximum value and the minimum value, respectively, of the fluorescence intensity in the second region. "A fluorescence intensity in a first region is lower than a fluorescence intensity in a second region" means that the maximum value and the minimum value of the fluorescence intensity in the first region are less than the maximum value and the minimum value, respectively, of the fluorescence intensity in the second region. The same is applied to the expression for relationship between a forward scattered light intensity in a first region and a forward scattered light intensity in a second region.

In the process step of step S102, the controller 51 counts the blood cells on the basis of the fluorescence intensity and the scattered light intensity in the measurement data. Specifically, the controller 51 identifies particles G1 in a range where white blood cells appear, particles G2 in a range where non-malaria-infected red blood cells appear, particles G3 in a range where malaria-infected red blood cells appear, particles G4 in a range where the single-ring form of red blood cells appear, and particles G5 in a range where the multi-ring form of red blood cells appear. In the scattergram 200, the range where white blood cells appear corresponds to the region 201, the range where non-malaria-infected red blood cells appear corresponds to the region 202, the range where malaria-infected red blood cells appear corresponds to the region 203, the range where the single-ring form of red blood cells appear corresponds to the region 204, and the range where the multi-ring form of red blood cells appear corresponds to the region 205. The controller 51 counts the identified particles in each region to obtain the number of blood cells in each region.

In the counting of the blood cells in step S102, the controller 51 counts the blood cells by data processing based on a procedure similar to the procedure in which the scattergram is generated and the regions are set, without generating the scattergram and setting the regions. However, the procedure is not limited thereto, and the controller 51 may generate the scattergram, set, in the generated scattergram, regions where the blood cells are distributed, and count the blood cells included in each of the set regions. The controller 51 does not generate the scattergram in order to count the blood cells. However, the controller 51 generates the scattergram when the screen described below is displayed on the display unit 53a.

In the scattergram 200, a region corresponding to gametocytes, a region corresponding to trophozoites, and a region corresponding to schizonts may be set. In this case, in step S102, the controller 51 may count the number of particles included in the range where the gametocytes appear, the number of particles included in the range where the trophozoites appear, and the number of particles included in the range where the schizonts appear.

Subsequently, in step S103, the controller 51 performs determination process described below with reference to FIG. 6. By the determination process, whether or not a blood specimen to be analyzed is infected with malaria is determined. Thus, the analysis is ended.

The inventors have found that, in a blood specimen collected from a subject who does not suffer from malaria, particles are sometimes distributed in the region 203 corresponding to the malaria-infected red blood cells. The inventors have found that, in the blood specimen collected from the subject who does not suffer from malaria, the particles distributed in the region 203 include an apoptotic body; a red blood cell including a Howell-Jolly body; or the like. The apoptotic body is a kind of extracellular vesicles. The Howell-Jolly body is a kind of inclusion bodies of nucleic acid. The inventors have found that an apoptotic body, and a red blood cell that includes a Howell-Jolly body are distributed from the region 204 corresponding to single-ring form of red blood cells, in such a direction that the fluorescence intensity and the forward scattered light intensity are enhanced.

Why the inventors have found that an apoptotic body, and a red blood cell that includes an Howell-Jolly body are distributed in the region 203 will be described below with reference to FIG. 12A to FIG. 15.

Thus, in a case where an apoptotic body or a red blood cell that includes a Howell-Jolly body is distributed in the region 203, if determination as malaria-positive is made because, for example, particles are distributed in the region 203, false-positive may occur. Therefore, the inventors have considered that whether or not the malaria-infected red blood cells are included is to be determined on the basis of variation of frequency distribution with respect to the fluorescence intensities. Hereinafter, in the determination process shown in FIG. 6, in a case where an apoptotic body or a red blood cell that includes a Howell-Jolly body is distributed in the region 203, malaria determination process is performed so as to reduce erroneous determination as malaria-positive.

Figure 6:
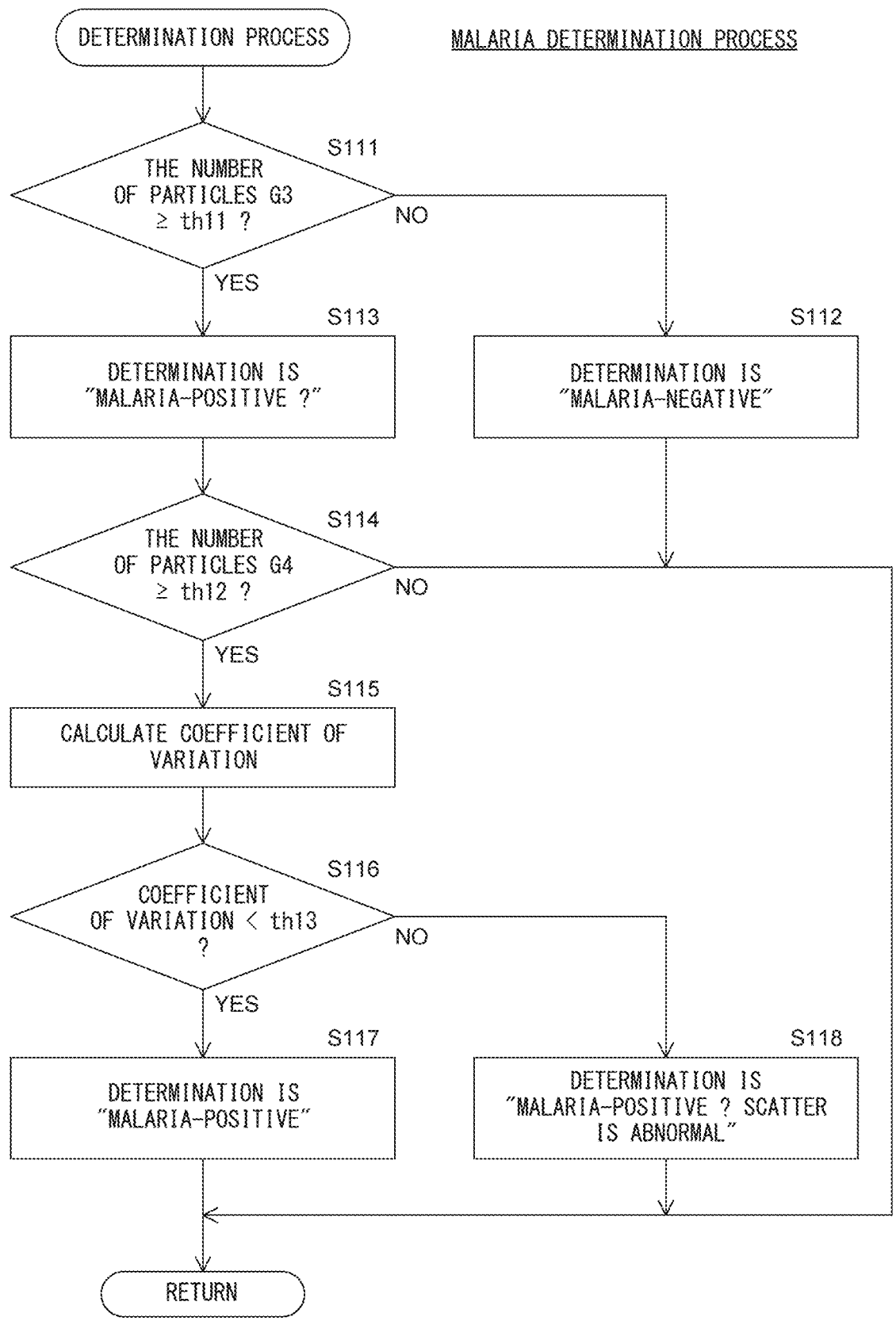
FIG. 6 is a flow chart showing a malaria determination process according to Embodiment 1.

As shown in FIG. 6, in step S111, the controller 51 determines whether or not the number of the particles G3 per unit volume is greater than or equal to a threshold value th11. As shown in FIG. 5B, the particles G3 represent particles included in the range where the malaria-infected red blood cells appear. The number of the particles G3 per unit volume is obtained by, for example, dividing the obtained number of the particles G3 by the volume of the first measurement sample that flows through the flow cell 101 while the first information is obtained. The threshold value th11 is set such that a blood specimen to be analyzed can be determined as "malaria-negative" on the basis of the number of the particles G3 per unit volume. The threshold value th11 is set to, for example, 200.

The volume used for the division in step S111 may be a volume of a blood specimen corresponding to the volume of the first measurement sample, instead of the volume of the first measurement sample. In step S111, the controller 51 may determine whether or not the number of the particles G3 is greater than or equal to a predetermined threshold value. The threshold value th11 can be changed through the input unit 54 by an operator. Threshold values th12, th13 described below, and threshold values th21, th22, th23, th31, th32 described below in Embodiments 2, 3 can be similarly changed through the input unit 54 by an operator. Thus, the operator is allowed to perform slight adjustment of the determination in each determination step.

When the number of the particles G3 per unit volume is less than the threshold value th11, the controller 51 determines, in step S112, that the blood specimen to be analyzed is "malaria-negative", and causes the storage unit 52 to store the determination result. The controller 51 ends the determination process.

Meanwhile, when the number of the particles G3 per unit volume is greater than or equal to the threshold value th11, the controller 51 determines the blood specimen to be analyzed as "malaria-positive?" in step S113, and causes the storage unit 52 to store the determination result. The determination result of "malaria-positive?" represents a state where, although the blood specimen to be analyzed is highly likely to include a malaria-infected red blood cell, it is difficult to determine the blood specimen to be analyzed as "malaria-positive".

Subsequently, in step S114, the controller 51 determines whether or not the number of the particles G4 per unit volume is greater than or equal to the threshold value th12. The particles G4 represent the particles included in the range where single-ring form of red blood cells appear, as shown in FIG. 5B. The number of the particles G4 per unit volume is obtained by, for example, dividing the obtained number of the particles G4 by the volume of the first measurement sample that flows through the flow cell 101 while the first information is obtained. The threshold value th12 is set such that, for the blood specimen to be analyzed, whether or not the malaria-infected red blood cells are distributed in the region 204 corresponding to the single-ring form of red blood cells, can be determined on the basis of the number of the particles G4 per unit volume. The threshold value th12 is set to, for example, 150.

The volume used for division in step S114 may be the volume of the blood specimen corresponding to the volume of the first measurement sample, instead of the volume of the first measurement sample. In step S114, the controller 51 may determine whether or not the number of the particles G4 is greater than or equal to a predetermined threshold value. The process step of step S114 may be omitted. However, since multiple particles are distributed particularly in the region 204 in the blood specimen infected with Plasmodium, the determination as to the number of the particles G4 is preferably performed in step S114.

In a case where the number of the particles G4 per unit volume is less than the threshold value th12, the controller 51 ends the determination process. In this case, the determination result is "malaria-positive?" which has been stored in step S113.

Meanwhile, in a case where the number of the particles G4 per unit volume is greater than or equal to the threshold value th12, the controller 51 calculates a value representing variation of a frequency distribution with respect to the fluorescence intensities of the particles G4 in step S115. Specifically, in step S115, the controller 51 calculates a coefficient of variation of the frequency distribution with respect to the fluorescence intensities of the particles G4. The value, representing variation of frequency distribution, calculated in step S115 may be the standard deviation, or a half-value width in the frequency distribution chart, as well as the coefficient of variation.

In the calculation of the coefficient of variation in step S115, the controller 51 calculates the coefficient of variation by data processing based on a procedure similar to the procedure in which the frequency distribution chart is generated, without generating the frequency distribution chart. However, the procedure is not limited thereto, and the controller 51 may generate the frequency distribution chart and calculate the coefficient of variation. The controller 51 does not generate the frequency distribution chart in order to calculate the coefficient of variation. However, the controller 51 generates the frequency distribution chart when the screen described below is displayed on the display unit 53a, and the controller 51 causes the display unit 53a to display the generated frequency distribution chart.

The value, representing the variation, calculated in step S115 may be a value that represents variation of a frequency distribution with respect to light intensities other than the fluorescence intensities. The value, representing the variation, calculated in step S115 is not limited to a value that represents variation of one-axis distribution, and may be a value that represents variation of two-axis or three-axis distribution, and may represent, for example, variation of a distribution on the scattergram 200. Instead of a combination of the fluorescence intensities and the forward scattered light intensities, the scattergram 200 may be generated on the basis of a combination of other light intensities.

Subsequently, in step S116, the controller 51 determines whether or not the coefficient of variation calculated in step S115 is less than the threshold value th13. The threshold value th13 is set such that a blood specimen to be analyzed can be determined as "malaria-positive" on the basis of the coefficient of variation. The threshold value th13 is set to, for example, 10%.

Although nucleic acid of the single-ring form of red blood cell is included in almost a certain amount, an amount of nucleic acid of an apoptotic body, and an amount of nucleic acid of a red blood cell including a Howell-Jolly body are various. Therefore, in a case where particles are distributed in the region 204 corresponding to the single-ring form of red blood cells, when the malaria-infected red blood cells are in the blood specimen, variation of the frequency distribution based on the particles G4 is small, and, when malaria-infected red blood cells are not in the blood specimen, variation of the frequency distribution based on the particles G4 is great. Therefore, by determining, in step S116, whether the coefficient of variation is great or small, whether the malaria-infected red blood cells are present or absent can be determined.

When the coefficient of variation is less than the threshold value th13, the controller 51 determines, in step S117, that the blood specimen to be analyzed is "malaria-positive", and causes the storage unit 52 to store the determination result. The controller 51 ends the determination process. In this case, the determination result is changed, from "malaria-positive?" which has been stored in step S113, to "malaria-positive".

Meanwhile, in a case where the coefficient of variation is greater than or equal to the threshold value th13, the determination of step S118 by the controller 51 is "malaria-positive? scatter is abnormal", and the controller 51 causes the storage unit 52 to store the determination result. In this case, "scatter is abnormal" in the determination result is information that indicates reliability of the determination result as to infection with Plasmodium. Specifically, "scatter is abnormal" is information that indicates that reliability of the determination result as to malaria is not high. The controller 51 ends the determination process.

In a case where the coefficient of variation is greater than or equal to the threshold value th13, malaria-infected red blood cells are less likely to be present. Therefore, it can be determined that malaria-infected red blood cells are not present. However, in this case, determination as "malaria-negative, scatter is abnormal" is preferably made without simply making determination as "malaria-negative".

Next, determination as to 10 kinds of specimens will be specifically described with reference to FIG. 7A to FIG. 9D.

Figure 7A:
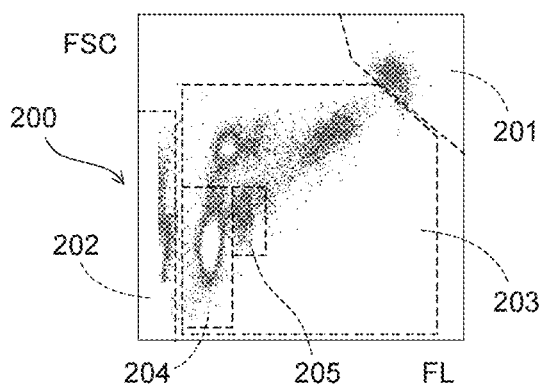
FIG. 7A illustrates a scattergram based on one specific kind of specimen, according to Embodiment 1.
Figure 7E:
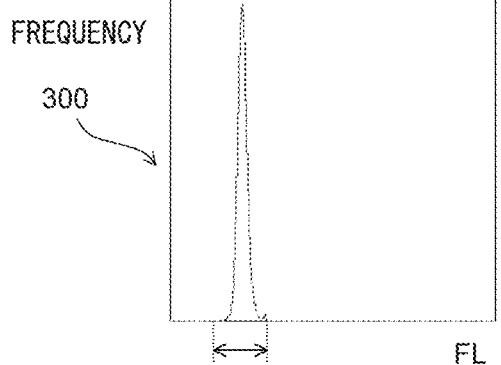
FIG. 7E illustrates a frequency distribution chart based on the one specific kind of specimen, according to Embodiment 1.
Figure 7B:
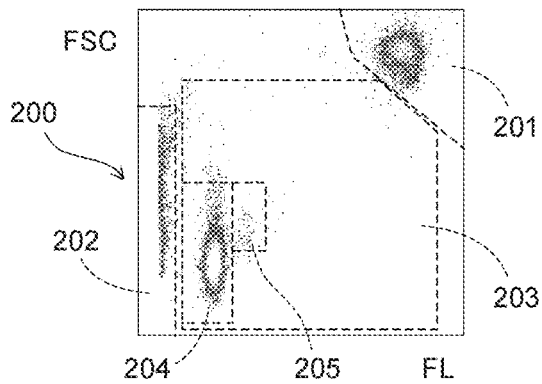
FIG. 7B illustrates a scattergram based on one specific kind of specimen, according to Embodiment 1.
Figure 7F:
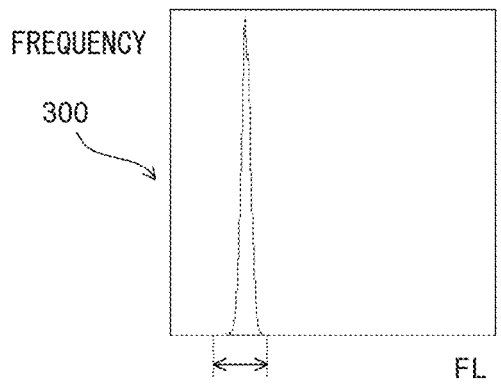
FIG. 7F illustrates a frequency distribution chart based on the one specific kind of specimen, according to Embodiment 1.
Figure 7C:
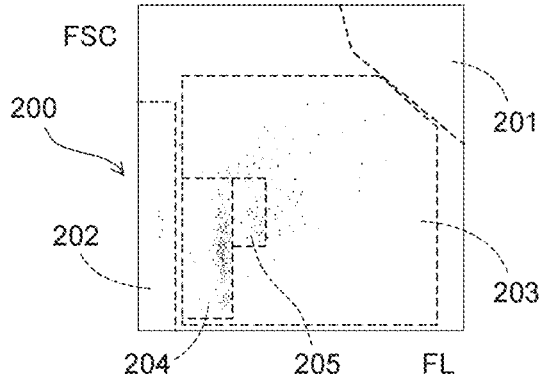
FIG. 7C illustrates a scattergram based on one specific kind of specimen, according to Embodiment 1.
Figure 7G:
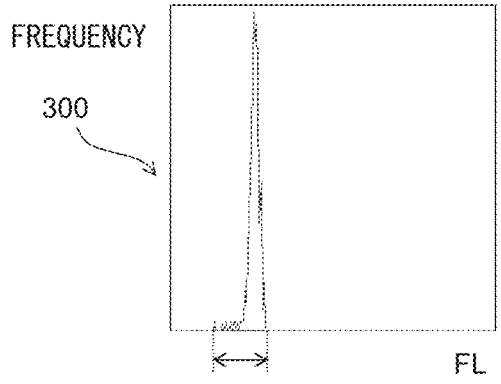
FIG. 7G illustrates a frequency distribution chart based on the one specific kind of specimen, according to Embodiment 1.
Figure 7D:
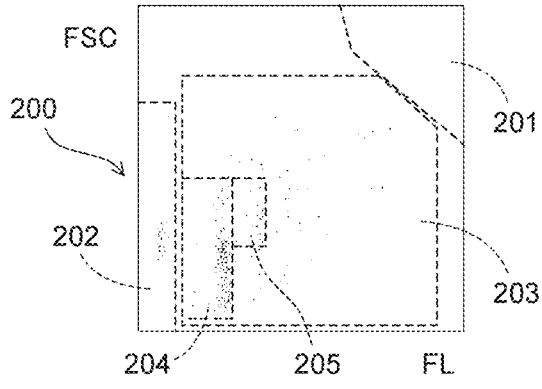
FIG. 7D illustrates a scattergram based on one specific kind of specimen, according to Embodiment 1.
Figure 7H:
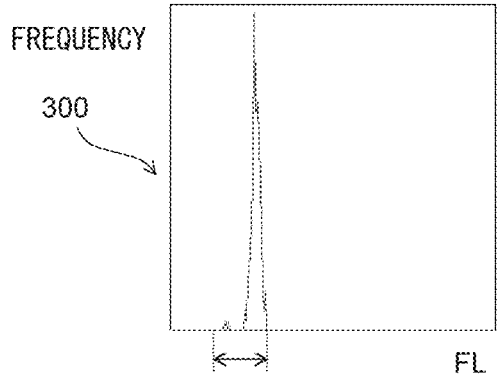
FIG. 7H illustrates a frequency distribution chart based on the one specific kind of specimen, according to Embodiment 1.
Figure 8A:
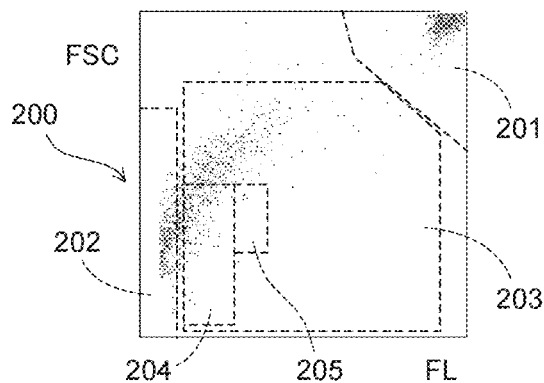
FIG. 8A illustrates a scattergram based on one specific kind of specimen, according to Embodiment 1.
Figure 8E:
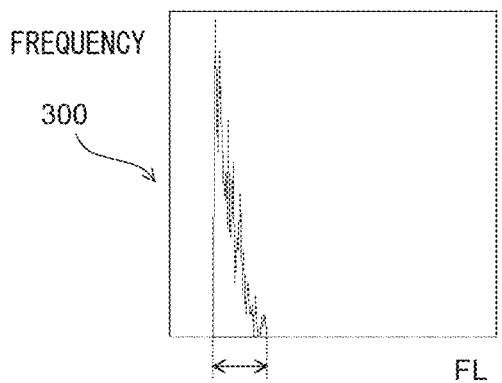
FIG. 8E illustrates a frequency distribution chart based on the one specific kind of specimen, according to Embodiment 1.
Figure 8B:
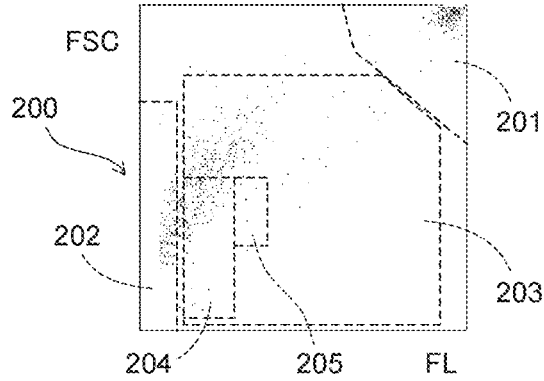
FIG. 8B illustrates a scattergram based on one specific kind of specimen, according to Embodiment 1.
Figure 8F:
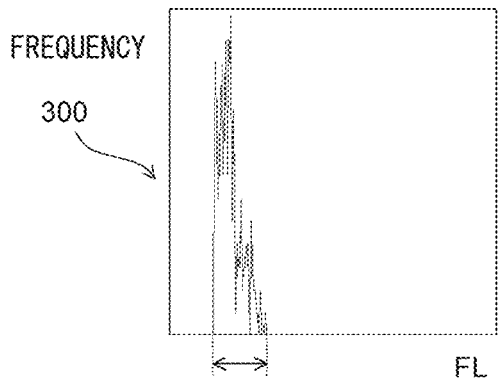
FIG. 8F illustrates a frequency distribution chart based on the one specific kind of specimen, according to Embodiment 1.
Figure 8C:
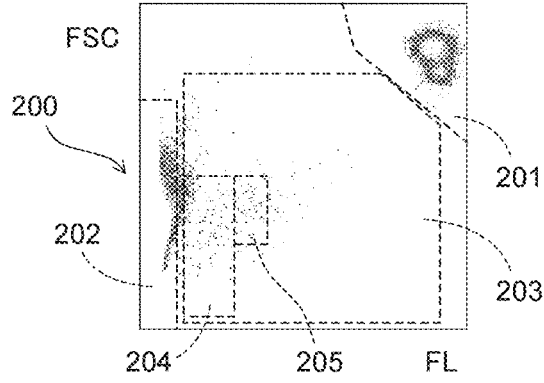
FIG. 8C illustrates a scattergram based on one specific kind of specimen, according to Embodiment 1.
Figure 8G:
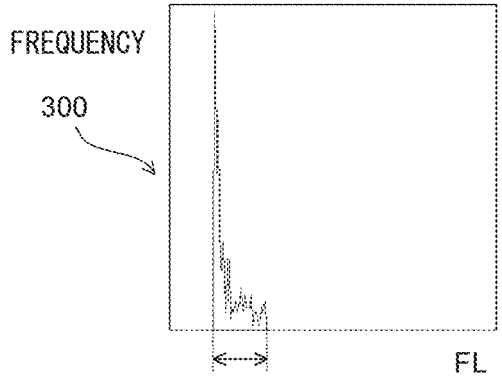
FIG. 8G illustrates a frequency distribution chart based on the one specific kind of specimen, according to Embodiment 1.
Figure 8D:
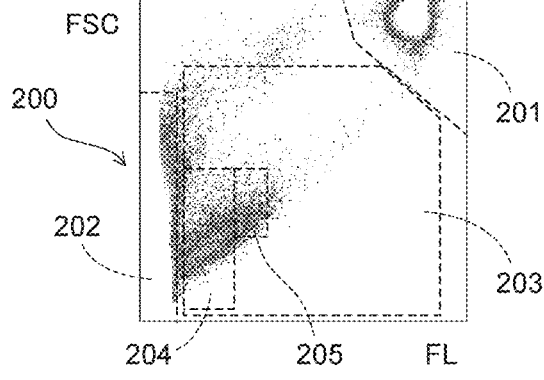
FIG. 8D illustrates a scattergram based on one specific kind of specimen, according to Embodiment 1.
Figure 8H:
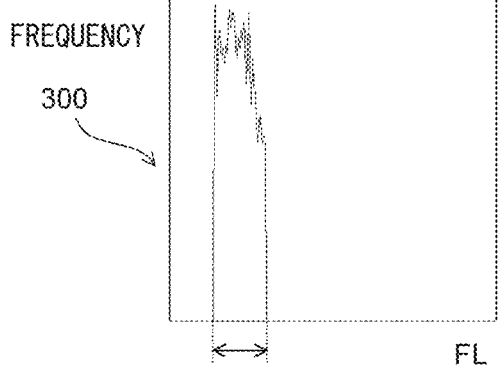
FIG. 8H illustrates a frequency distribution chart based on the one specific kind of specimen, according to Embodiment 1.
Figure 9A:
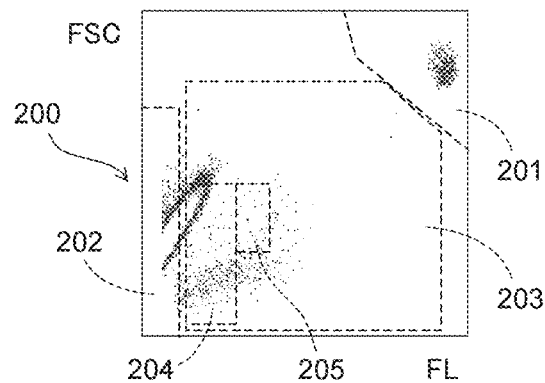
FIG. 9A illustrates a scattergram based on one specific kind of specimen, according to Embodiment 1.
Figure 9C:
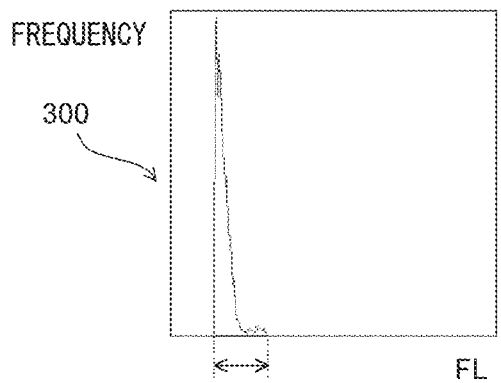
FIG. 9C illustrates a frequency distribution chart based on the one specific kind of specimen, according to Embodiment 1.
Figure 9B:
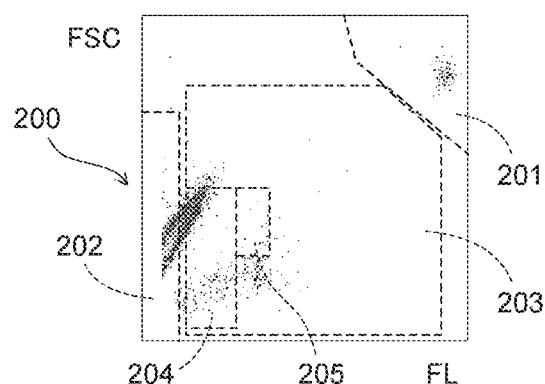
FIG. 9B illustrates a scattergram based on one specific kind of specimen, according to Embodiment 1.
Figure 9D:
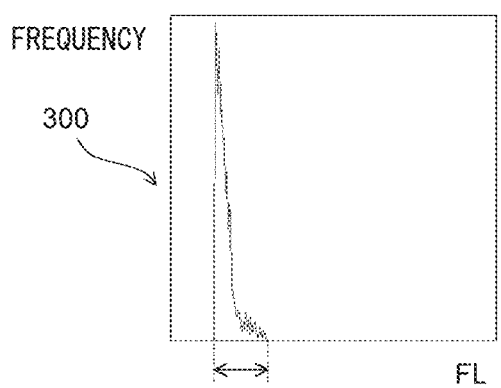
FIG. 9D illustrates a frequency distribution chart based on the one specific kind of specimen, according to Embodiment 1.

FIGS. 7A, 7B each show the scattergram 200 based on a blood specimen collected from a subject who suffers from malaria. FIGS. 7C, 7D each show the scattergram 200 based on cultured malaria. FIGS. 8A, 8B each show the scattergram 200 obtained when apoptosis is induced to a Jurkat cell. FIGS. 8C, 8D each show the scattergram 200 based on a blood specimen collected from a subject who does not suffer from malaria. FIGS. 9A, 9B each show the scattergram 200 based on a blood specimen collected from a mouse that is not infected with malaria. In any case, particles on the left end of the region 202 are regarded as noise components, and eliminated.

A red blood cell that includes a Howell-Jolly body is always included in the blood specimen collected from a mouse. In the following description for the determination, the blood specimen collected from the mouse is used as an example of a blood specimen, of a person, which includes a red blood cell including a Howell-Jolly body.

In any of the 10 kinds of specimens shown in FIGS. 7A to 7D, FIGS. 8A to 8D, FIGS. 9A, 9B, a certain number of particles appear in each of the region 203 corresponding to malaria-infected red blood cells and the region 204 corresponding to the single-ring form of red blood cells. In FIGS. 7A to 7D, FIGS. 8A to 8D, FIGS. 9A, 9B, the numbers of the particles G4 are 18768, 8208, 262, 204, 373, 215, 359, 5923, 4037, 1147, respectively. Therefore, in the determination process shown in FIG. 6, determination of steps S111, S114 is YES, and the coefficient of variation of the frequency distribution with respect to the fluorescence intensities of the particles G4 is calculated in step S115.

FIGS. 7E to 7H, FIGS. 8E to 8H, FIGS. 9C, 9D show frequency distribution charts 300 generated based on the scattergrams 200 in FIGS. 7A to 7D, FIGS. 8A to 8D, FIGS. 9A, 9B, respectively. In each frequency distribution chart 300, the horizontal axis represents a fluorescence intensity and the vertical axis represents frequency. The frequency distribution chart 300 indicates a frequency distribution based on only the particles G4 in a range where the single-ring form of red blood cells appear. The frequency distribution chart 300 is normalized based on a value of the greatest frequency.

With reference to the frequency distribution chart 300 in each of FIGS. 7E to 7H, the frequency distribution forms a sharp shape in any case. The coefficients of variation in FIGS. 7E to 7H are 7.3%, 6.4%, 7.4%, 6.3%, respectively. Therefore, in any of the cases shown in FIGS. 7E to 7H, determination of step S116 shown in FIG. 6 is YES, and these specimens are determined as "malaria-positive". The specimen shown in each of FIGS. 7E to 7H is the specimen that is infected with malaria, as described above. Therefore, it is understood that, in the determination process shown in FIG. 6, for these four specimens, appropriate determination result as "malaria-positive" can be obtained.

Meanwhile, with reference to the frequency distribution chart 300 in each of FIGS. 8E to 8H, FIGS. 9C, 9D, the frequency distribution does not form a completely sharp shape in any case. The coefficients of variation in FIGS. 8E to 8H, FIGS. 9C, 9D are 19.6%, 18.8%, 25.1%, 21.1%, 16.5%, 18.0%, respectively. Therefore, in any of cases shown in FIGS. 8E to 8H, FIGS. 9C, 9D, determination of step S116 shown in FIG. 6 is NO, and these specimens are determined as "malaria-positive? scatter is abnormal". The specimen shown in each of FIGS. 8E to 8H, FIGS. 9C, 9D is the specimen that is not infected with malaria. Therefore, it is understood that, in the determination process shown in FIG. 6, these six specimens can be prevented from being erroneously determined as "malaria-positive".

As described above, in the determination process shown in FIG. 6, in a case where malaria-infected red blood cells are not in the blood specimen, even if particles are in the region 203 or the region 204, erroneous determination as "malaria-positive" can be avoided and appropriate determination as "malaria-positive? scatter is abnormal" can be made. In a case where malaria-infected red blood cells are in the blood specimen, appropriate determination as "malaria-positive" can be made. Therefore, false-positive is inhibited from occurring and whether or not infection with Plasmodium has occurred can be determined with enhanced accuracy.

In a case where a person suffers from malaria, the function of the spleen may reduce, and a red blood cell that includes a Howell-Jolly body may be always included in the blood specimen. In this case, both malaria-infected red blood cells and the red blood cell that includes the Howell-Jolly body are in the blood specimen. However, determination of step S111 shown in FIG. 6 is YES, and the determination result can be prevented from being "malaria-negative".

Next, a screen 60 displayed on the display unit 53a in step S27 shown in FIG. 4 will be described.

Figure 10:
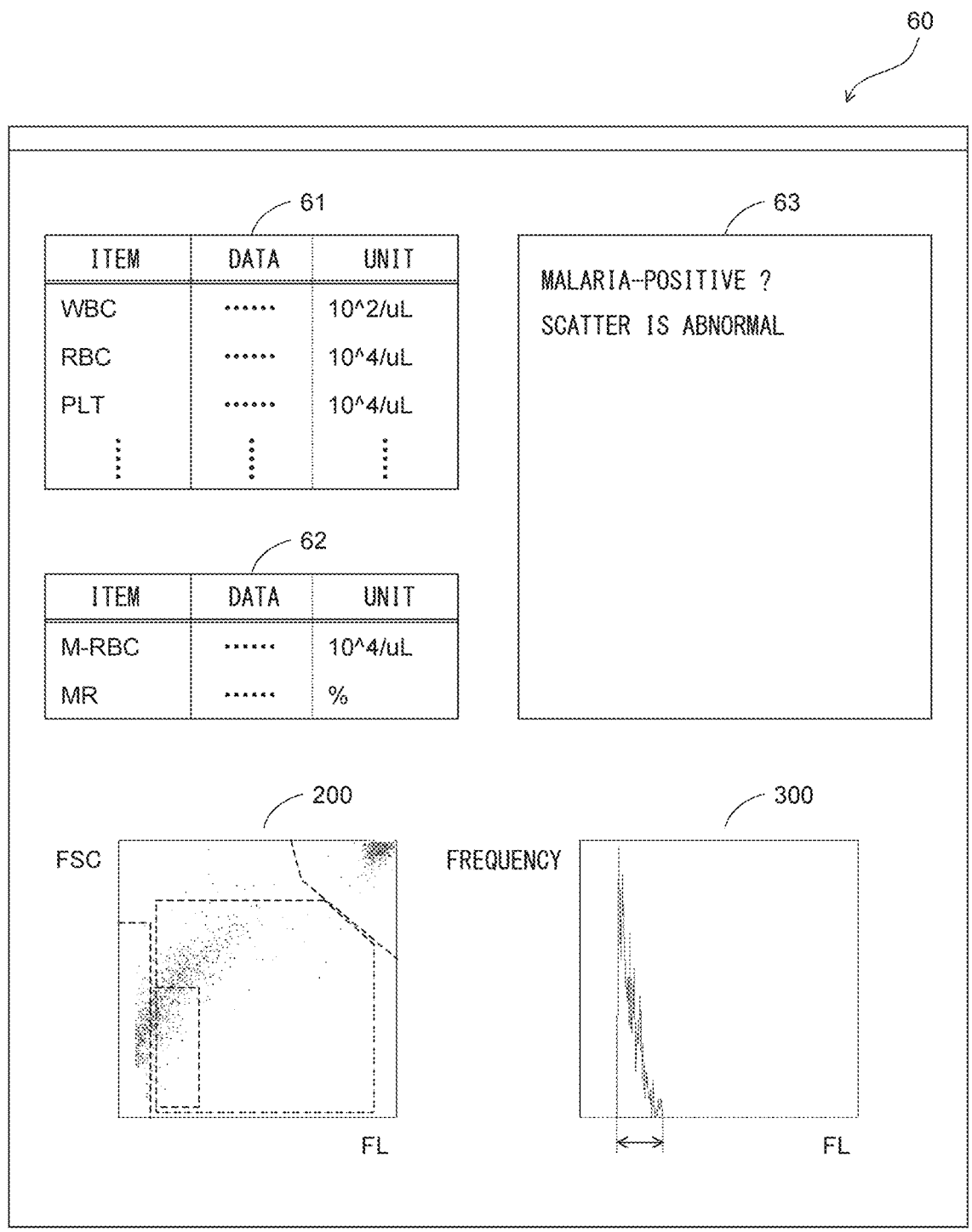
FIG. 10 is a schematic diagram illustrating a configuration of a screen displayed on a display unit according to Embodiment 1.

As shown in FIG. 10, the screen 60 includes list regions 61, 62, a comment region 63, the scattergram 200, and the frequency distribution chart 300. In the list region 61, the results of counting of white blood cells, red blood cells, platelets, and the like are displayed in the form of a list. In the list region 62, results of counting of malaria-infected red blood cells and a proportion of the malaria-infected red blood cells are displayed. The proportion of malaria-infected red blood cells is obtained by dividing the number of blood cells in the region 203 corresponding to malaria-infected red blood cells as shown in FIG. 5B, by the number of red blood cells obtained in step S101 shown in FIG. 5A.

In the comment region 63, the determination result obtained in the determination process shown in FIG. 6 is displayed. Specifically, in a case where step S112 in FIG. 6 is performed, nothing is displayed in the comment region 63. Also in this case, "malaria-negative" may be displayed in the comment region 63. In a case where the determination of step S114 shown in FIG. 6 is NO, "malaria-positive?" is displayed in the comment region 63. In a case where step S117 in FIG. 6 is performed, "malaria-positive" is displayed in the comment region 63. In a case where step S118 in FIG. 6 is performed, "malaria-positive? scatter is abnormal" is displayed in the comment region 63 as illustrated in FIG. 10.

When "malaria-positive" or "malaria-negative" is displayed in the comment region 63, a doctor or the like can determine whether or not the subject suffers from malaria, and determine whether or not a subject under treatment has been completely cured of malaria. When "malaria-positive?" is displayed in the comment region 63, a doctor or the like can know that the subject is likely to suffer from malaria. In this case, the doctor or like can perform additional test such as checking of the blood specimen with the use of a microscope.

When "scatter is abnormal" is displayed in the comment region 63, a doctor or the like can know that reliability of the determination result as to whether or not malaria has occurred, is not high. The doctor or the like can know that particles, such as extracellular vesicles, or red blood cells that include inclusion bodies of nucleic acid, other than malaria-infected red blood cells are likely to be distributed in the region 203 in the scattergram 200. In this case, the doctor or the like can perform additional test such as checking of the blood specimen with the use of a microscope. By the scattergram 200 and the frequency distribution chart 300 being displayed on the screen 60, a doctor or the like is allowed to quickly know the state of the blood specimen in detail.

Next, verification of the determination process performed by the inventors will be described.

The inventors made change in the determination process of Embodiment 1 shown in FIG. 6 such that step S114 was omitted and determination as "malaria-negative" was made in step S118, and performed this process as determination process of verification example 1. That is, in the determination process of verification example 1, in a case where the determinations of steps S111, S116 were both YES, the determination result was "malaria-positive", and, in a case where one of the determinations in steps S111, S116 was NO, the determination result was "malaria-negative".

The inventors made change in the determination process of Embodiment 1 shown in FIG. 6 such that steps S114 to S118 were omitted and determination as "malaria-positive" was made in step S113, and performed this process as determination process of verification example 2. That is, in the determination process of verification example 2, in a case where the determination of step S111 was YES, the determination result was "malaria-positive" and, in a case where the determination of step S111 was NO, the determination result was "malaria-negative".

The inventors used 27 malaria-positive specimens and 130 malaria-negative specimens, prepared the first measurement samples based on these specimens, and measured the prepared first measurement samples by using the optical detection unit 41. The inventors performed analysis shown in FIG. 5A by using measurement data obtained in the first measurement, and performed determination as to malaria by the determination processes of verification examples 1, 2 as set above. The inventors determined whether or not determination as to malaria was appropriately made, on the basis of the determination results, as to malaria, obtained in the determination processes of verification examples 1, 2, thereby performing verification. In the verification, the regions of the scattergram 200 shown in FIG. 5B were slightly adjusted for each specimen by using an automatic demarcation algorithm. In the verification, the threshold value th11 in step S111 was set to 30 and the threshold value th13 in step S116 was set to 20%.

As shown in FIG. 11A, in verification example 1, all of the 27 malaria-positive specimens were appropriately determined as malaria-positive. Among the 130 malaria-negative specimens, although two specimens were erroneously determined as malaria-positive, 128 specimens were appropriately determined as malaria-negative. According to the results, in verification example 1, sensitivity was 27/27=100% and specificity was 128/130=98.5%.

Subsequently, as shown in FIG. 11B, in verification example 2, all of the 27 malaria-positive specimens were appropriately determined as malaria-positive. Among the 130 malaria-negative specimens, although 48 specimens were appropriately determined as malaria-negative, 82 specimens were erroneously determined as malaria-positive. According to the results, in verification example 2, sensitivity was 27/27=100% and specificity was 48/130=36.9%.

According to the results in FIGS. 11A, 11B, it can be understood that, in the determination process of verification example 1, specificity can be greatly improved as compared to the determination process of verification example 2. Therefore, in the determination process of Embodiment 1 shown in FIG. 6, since the determination of step S116 using the coefficient of variation is performed in addition to the determination of step S111, it can be said that specificity is improved to inhibit false-positive from occurring.

<Study of Red Blood Cell Including Inclusion Body of Nucleic Acid, and Extracellular Vesicle>

Why the inventors have found that an apoptotic body which is a kind of extracellular vesicles, and a red blood cell including a Howell-Jolly body that is a kind of inclusion bodies of nucleic acid are distributed in the region 203, shown in FIG. 5B, corresponding to malaria-infected red blood cells, will be described. The red blood cell including an inclusion body of nucleic acid is a red blood cell including an inclusion body, of nucleic acid, which is left after nucleic acid has been agglutinated inside a cell. As to a reticulocyte, RNAs thereinside are dispersed in the reticulocyte, and nucleic acid does not exist in the agglutinated form. Therefore, the reticulocyte is different from a red blood cell including an inclusion body of nucleic acid.

Firstly, the inventors checked the determination method in which the determination result as to malaria was positive in a case where particles were distributed in the region 203 corresponding to malaria-infected red blood cells, and found that, although a subject did not suffer from malaria, the determination result as to malaria was sometimes positive, that is, so-called false-positive sometimes occurred. That is, the inventors have found that, although a subject does not suffer from malaria, particles are distributed in the region 203 corresponding to the malaria-infected red blood cells in some cases.

Next, the inventors performed the following observation and experiment for a case where particles were distributed in the region 203 although a subject did not suffer from malaria.

The inventors observed, by using a microscope, the blood specimen that had particles distributed in the region 203 although the subject did not suffer from malaria, that is, the blood specimen from which false-positive was caused.

Figure 12A:
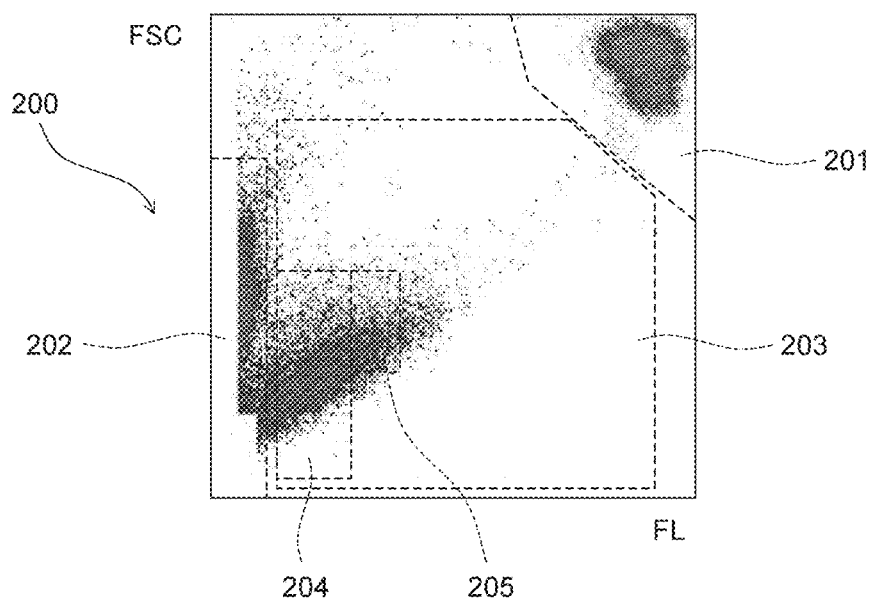
FIG. 12A illustrates a scattergram based on a blood specimen from which false-positive is caused, according to Embodiment 1.
Figure 12B:
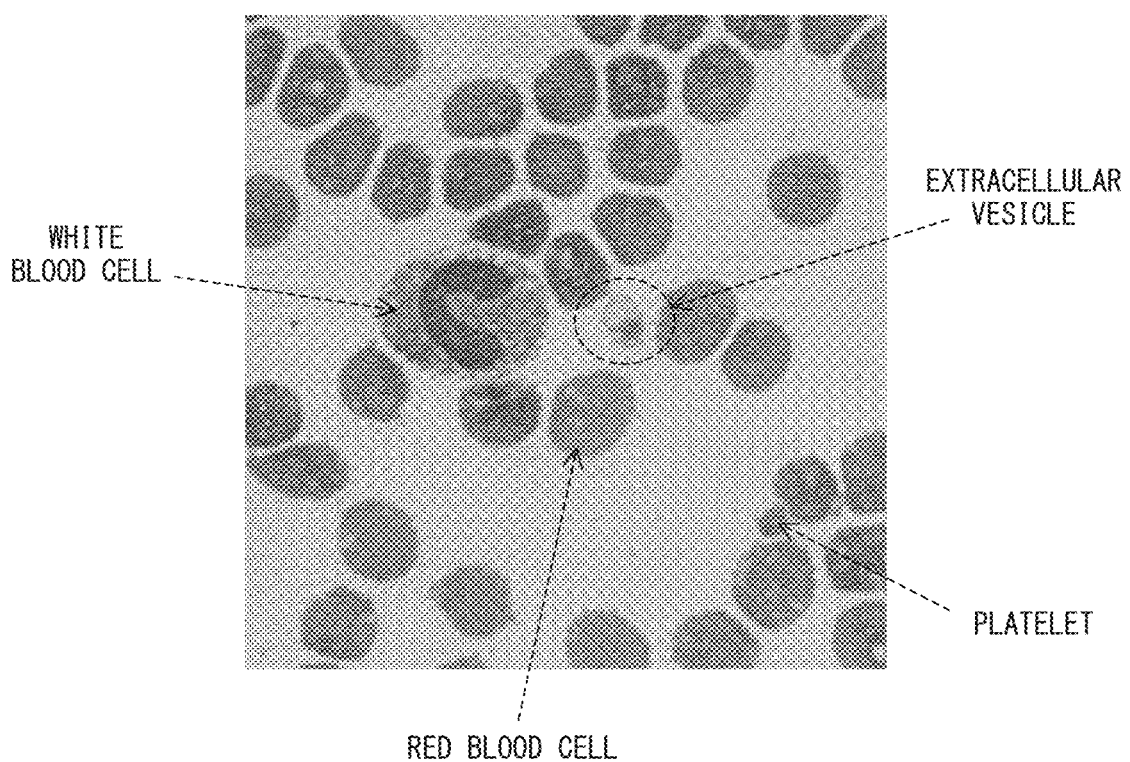
FIG. 12B illustrates an image obtained when the blood specimen from which false-positive is caused is observed by using a microscope, according to Embodiment 1.

FIG. 12A shows the scattergram 200 generated based on the blood specimen from which false-positive is caused. As shown in FIG. 12A, particles are distributed in the region 203 from the originating point in the diagonal direction. That is, the particles are distributed in the region 203 along a straight line representing a proportional relationship between the fluorescence intensity and the forward scattered light intensity. FIG. 12B shows an image representing a result of the blood specimen shown in FIG. 12A being observed by using a microscope. As shown in FIG. 12B, a particle which is different from any of a red blood cell, a white blood cell, and a platelet and which has nearly the same size as the platelet, is included in the blood specimen together with red blood cells, white blood cells, and platelets. The inventors considered that the particle is highly likely to be an extracellular vesicle.

Figure 13A:
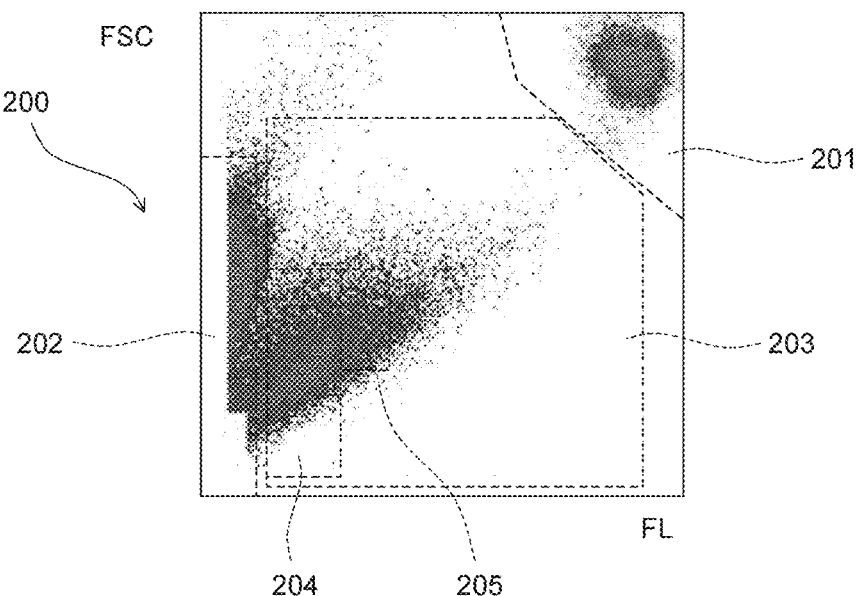
FIG. 13A illustrates a scattergram based on a blood specimen from which false-positive is caused, according to Embodiment 1.
Figure 13B:
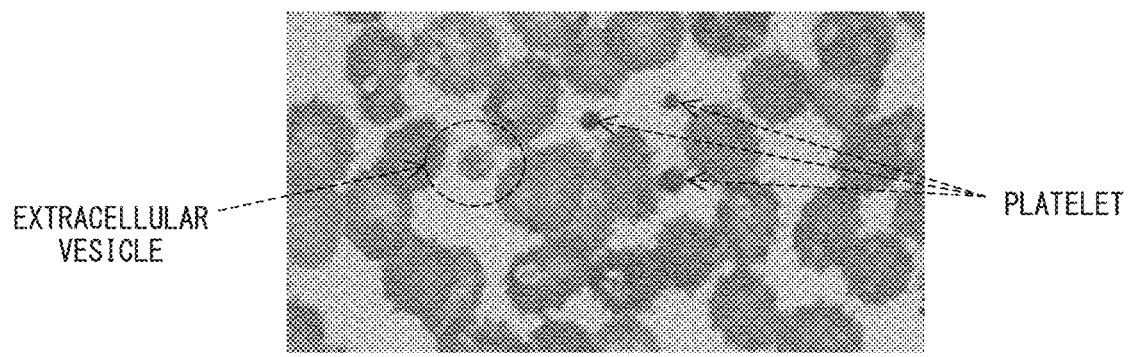
FIG. 13B illustrates an image obtained when the blood specimen from which false-positive is caused is observed by using a microscope, according to Embodiment 1.
Figure 13C:
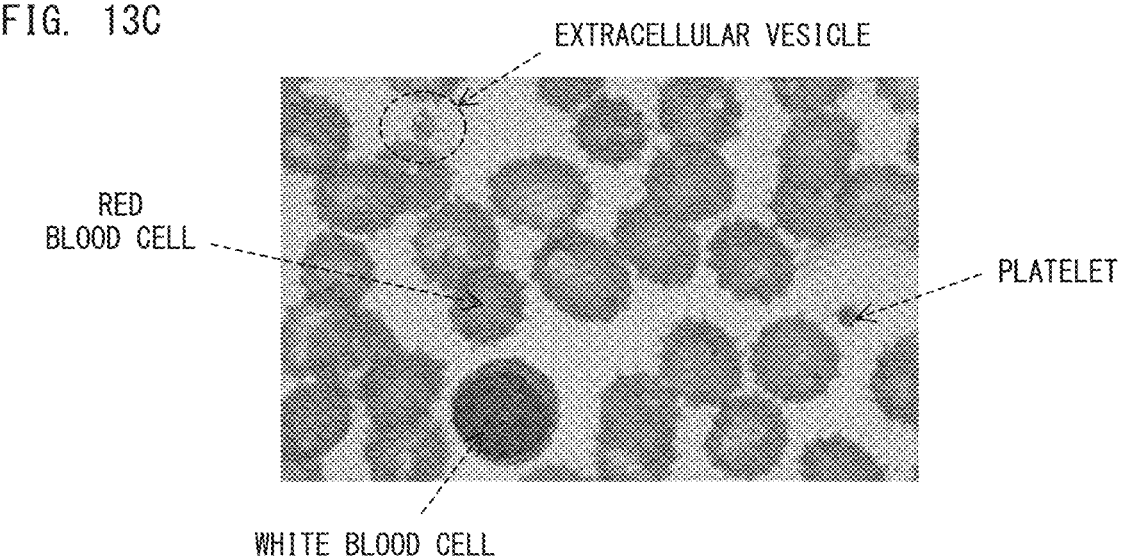
FIG. 13C illustrates an image obtained when the blood specimen from which false-positive is caused is observed by using a microscope, according to Embodiment 1.

FIG. 13A shows the scattergram 200 generated based on another blood specimen from which false-positive is caused. As shown in FIG. 13A, also in the blood specimen, particles are distributed in the region 203 from the originating point in the diagonal direction. FIGS. 13B, 13C each show an image representing a result of the blood specimen shown in FIG. 13A being observed by using a microscope. As shown in FIGS. 13B, 13C, also in the blood specimen, particles which may be extracellular vesicles are included together with red blood cells, white blood cells, and platelets.

According to the results shown in FIG. 12A to FIG. 13C, it has been found that a particle which may be an extracellular vesicle is in the blood specimen that has particles distributed in the region 203 although the subject does not suffer from malaria.

The inventors have performed the following experiment. In the experiment, apoptosis is induced to a Jurkat cell and how an apoptotic body that is a kind of extracellular vesicles appears in the scattergram 200 is confirmed. The conditions for the experiment are as follows:

(Jurkat Cell)
Medium: 10% FBS-added RPMI1640 medium
Cell solution: Jurkat cells that were cultured to about $1\times10^6/\mu L$ were 10-fold diluted in the medium, and cultured for 24 hours.
(Induction of apoptosis)
Inducer: 1 µM Staurosporine
Stock solution: 250 µg/500 µL DMSO (1 mM Staurosporine)
100 µM Staurosporine solution was generated by 10-fold dilution of 1 mM Staurosporine in the medium, and added in an amount of 1/100 per culture medium.

FIG. 14A shows the scattergram 200 generated based on the Jurkat cells to which apoptosis had not been induced yet. Malaria-infected red blood cells were not in the Jurkat cells. Therefore, as shown in FIG. 14A, particles were not substantially distributed in the region 203 of the scattergram 200. Meanwhile, FIG. 14B shows the scattergram 200 generated based on the Jurkat cells that were observed when four hours had elapsed after induction of apoptosis to the Jurkat cells shown in FIG. 14A.

It is known that apoptosis reaction progresses for some period after apoptosis is induced. In FIG. 14B, particles distributed from the originating point in the diagonal direction appeared after the apoptosis was induced, and are thus regarded as apoptotic bodies that are a kind of extracellular vesicles. Also in the scattergram 200 shown in each of FIG. 12A and FIG. 13A, it can be confirmed that multiple particles were distributed in a region corresponding to the region, shown in FIG. 14B, where the apoptotic bodies were distributed.

Next, the inventors observed, by using a microscope, the blood specimen on the scattergram 200 shown in FIG. 9A, as a blood specimen that had particles distributed in the region 203 although a subject did not suffer from malaria. The blood specimen shown in FIG. 9A is a blood specimen collected from a mouse which is not infected with malaria.

Figure 15:
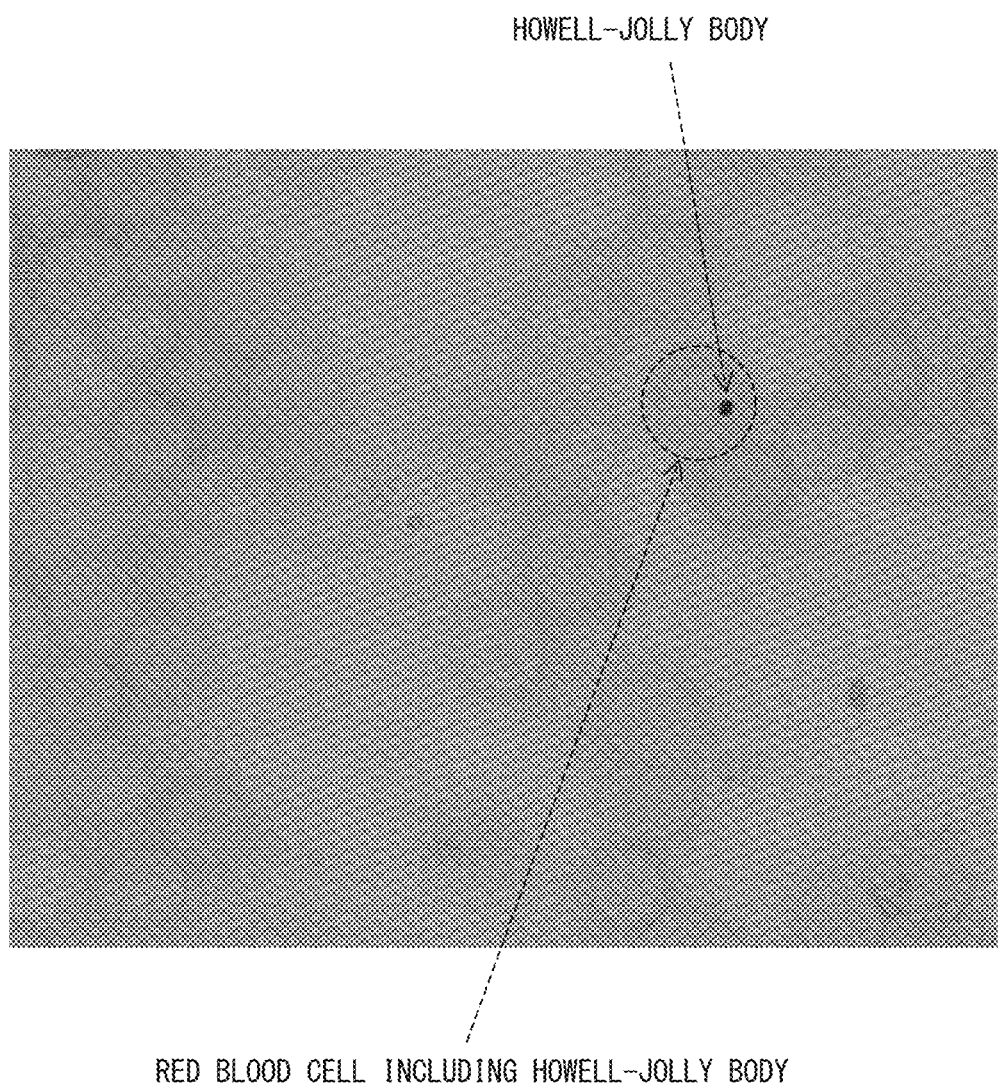
FIG. 15 illustrates an image obtained when a blood specimen, of a mouse, from which false-positive is caused, is observed by using a microscope, according to Embodiment 1.

FIG. 15 shows an image representing a result of the blood specimen, of the mouse, shown in FIG. 9A being observed by using a microscope. As shown in FIG. 15, in the blood specimen of the mouse, a red blood cell including a Howell-Jolly body was included together with normal mature red blood cells. In the scattergram 200 generated based on the blood specimen of the mouse, as shown in FIG. 9A, a particle was distributed in the region 203, and the particles were distributed in the region 203 from the originating point in the diagonal direction. According to the above description, the inventors have considered that, in some cases, a red blood cell that includes a Howell-Jolly body may also be in a human blood specimen which has particles distributed in the region 203 although the subject does not suffer from malaria.

According to the results of the above-described observation and experiment, the inventors have found that an apoptotic body, and a red blood cell including a Howell-Jolly body are distributed along a straight line representing a proportional relationship between the fluorescence intensity and the forward scattered light intensity. The inventors have found that, in a case where particles appear in the region 203 corresponding to malaria-infected red blood cells although the subject does not suffer from malaria, the particles include an apoptotic body which is a kind of extracellular vesicles, or a red blood cell including a Howell-Jolly body which is a kind of inclusion bodies of nucleic acid.

The inventors have found that variation of the frequency distribution with respect to the fluorescence intensities of the particles G4 in the region 204 is great in a case where at least one of a red blood cell including an inclusion body of nucleic acid, and an extracellular vesicle is distributed in the region 204, and the variation is small in a case where malaria-infected red blood cells are distributed in the region 204.

In a case where malaria-infected red blood cells are included in a blood specimen, only one mountain-shaped portion where the frequency is significantly high is likely to appear in the frequency distribution based on the particles G4. Meanwhile, in the case of a blood specimen from which false-positive is caused, red blood cells that include inclusion bodies of nucleic acid, or extracellular vesicles are distributed, in a wide range of the fluorescence intensities, in the frequency distribution based on the particles G4, and difference of frequency is less likely to increase. Therefore, in a case where the frequency distribution with respect to the fluorescence intensities is generated on the basis of the particles G4, variation of the frequency distribution becomes greatly different between a blood specimen that includes malaria-infected red blood cells and a blood specimen from which false-positive is caused. Therefore, discrimination between malaria-positive and false-positive can be clearly made according to variation of the frequency distribution of the particles G4 included in a range where single-ring form of red blood cells appear.

According to the above-described finding, the inventors have considered the malaria determination process as shown in FIG. 6 in order to inhibit false-positive from occurring.

An extracellular vesicle is a vesicle that is released from a cell, and conceptually includes a fine particle derived from a nucleated cell and a fine particle derived from a non-nucleated cell. Examples of the extracellular vesicle include exosomes, microvesicles (MV), apoptotic bodies, and the like. In consideration of the size of the particle, a part of microvesicles in addition to the apoptotic bodies is likely to be distributed in the region 203. Examples of a red blood cell including an inclusion body of nucleic acid include a Howell-Jolly body, basophilic stippling, and the like. In other words, examples of the inclusion body of nucleic acid conceptually include a Howell-Jolly body and basophilic stippling. Basophilic stippling is also a kind of inclusion bodies of nucleic acid. Red blood cells that include basophilic stippling in addition to red blood cells that include Howell-Jolly bodies are likely to be distributed in the region 203. Therefore, by determining variation with respect to the fluorescence intensities of the particles G4 as described above, whether various extracellular vesicles are present or absent, and whether red blood cells that include various inclusion bodies of nucleic acid are present or absent, can be also determined.

Embodiment 2

Figure 16:
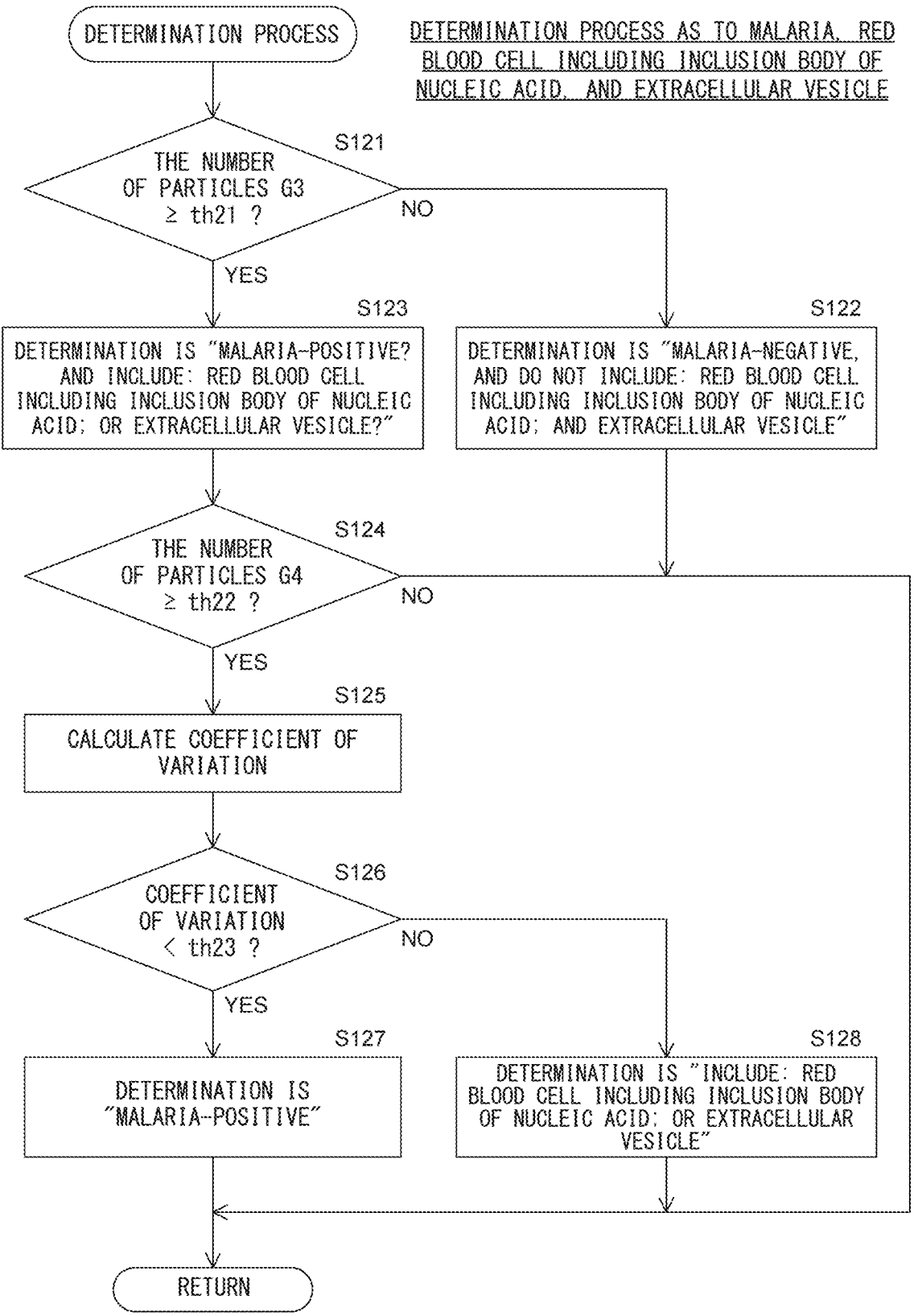
FIG. 16 is a flow chart showing a determination process as to malaria; a red blood cell including an inclusion body of nucleic acid, and an extracellular vesicle, according to Embodiment 2.

According to Embodiment 2, in the determination process, not only whether or not malaria has occurred, but also whether at least one of a red blood cell including an inclusion body of nucleic acid, and an extracellular vesicle is present or absent is determined. In Embodiment 2 and Embodiment 3 described below, "whether at least one of: a red blood cell including an inclusion body of nucleic acid; and an extracellular vesicle is present or absent is determined" means that whether either a red blood cell including an inclusion body of nucleic acid, or an extracellular vesicle is present or absent is determined, that is, whether or not at least one of a red blood cell including an inclusion body of nucleic acid, and an extracellular vesicle is present is determined. The determination process of Embodiment 2 is different from the determination process of Embodiment 1 shown in FIG. 6 in contents to be determined. However, as shown in FIG. 16, the configuration is substantially the same therebetween. The other configuration of Embodiment 2 is the same as for Embodiment 1.

As shown in FIG. 16, in step S121, the controller 51 determines whether or not the number of the particles G3 per unit volume is greater than or equal to the threshold value th21. The particles G3 are particles in a range where malaria-infected red blood cells appear, as shown in FIG. 5B. The threshold value th21 is set such that it can be determined that a blood specimen to be analyzed is "malaria-negative, and does not include: a red blood cell including an inclusion body of nucleic acid; and an extracellular vesicle", on the basis of the number of the particles G3 per unit volume. The threshold value th21 is set to, for example, the same value as the threshold value th11 in step S111 in FIG. 6.

When the number of the particles G3 per unit volume is less than the threshold value th21, the controller 51 determines, in step S122, that the blood specimen to be analyzed is "malaria-negative, and does not include: a red blood cell including an inclusion body of nucleic acid; and an extracellular vesicle", and causes the storage unit 52 to store the determination result. The controller 51 ends the determination process.

Meanwhile, when the number of the particles G3 per unit volume is greater than or equal to the threshold value th21, the controller 51 determines, in step S123, that the blood specimen to be analyzed is "malaria-positive? and includes: a red blood cell including an inclusion body of nucleic acid; or an extracellular vesicle?", and causes the storage unit 52 to store the determination result. The determination result of "malaria-positive? and includes: a red blood cell including an inclusion body of nucleic acid; or an extracellular vesicle?" means that the blood specimen to be analyzed is highly likely to include at least one of malaria-infected red blood cells, and a red blood cell including an inclusion body of nucleic acid, or an extracellular vesicle, but it is difficult to determine which is included in the blood specimen to be analyzed.

Subsequently, in step S124, the controller 51 determines whether or not the number of the particles G4 per unit volume is greater than or equal to the threshold value th22. The particles G4 are particles included in a range where the single-ring form of red blood cells appear as shown in FIG. 5B. The threshold value th22 is set such that, for the blood specimen to be analyzed, whether a malaria-infected red blood cell, a red blood cell including an inclusion body of nucleic acid, or an extracellular vesicle is distributed in the region 204 corresponding to the single-ring form of red blood cells, on the basis of the number of the particles G4 per unit volume. The threshold value th22 is set to, for example, the same value as the threshold value th12 in step S114 shown in FIG. 6.

When the number of the particles G4 per unit volume is less than the threshold value th22, the controller 51 ends the determination process. In this case, the determination result is "malaria-positive? and includes: a red blood cell including an inclusion body of nucleic acid; or an extracellular vesicle?" which has been stored in step S123.

Meanwhile, when the number of the particles G4 per unit volume is greater than or equal to the threshold value th22, the controller 51 calculates, in step S125, a value representing variation of the frequency distribution with respect to the fluorescence intensities of the particles G4. Specifically, in step S125, the controller 51 calculates the coefficient of variation of the frequency distribution with respect to the fluorescence intensities of the particles G4. The value, representing variation of the frequency distribution, calculated in step S125 may be the standard deviation, or a half-value width in the frequency distribution chart, as well as the coefficient of variation.

Subsequently, in step S126, the controller 51 determines whether or not the coefficient of variation calculated in step S125 is less than the threshold value th23. The threshold value th23 is set such that it can be determined that a blood specimen to be analyzed is "malaria-positive" or "includes: a red blood cell including an inclusion body of nucleic acid; or an extracellular vesicle", on the basis of the coefficient of variation. The threshold value th23 is set to, for example, the same value as the threshold value th13 in step S116 shown in FIG. 6.

When the coefficient of variation is less than the threshold value th23, the controller 51 determines, in step S127, that the blood specimen to be analyzed is "malaria-positive" and causes the storage unit 52 to store the determination result. The controller 51 ends the determination process. In this case, the determination result is changed from "malaria-positive? and includes: a red blood cell including an inclusion body of nucleic acid; or an extracellular vesicle?" which has been stored in step S123 to "malaria-positive".

In step S127, the controller 51 may determine "malaria-positive. Includes: a red blood cell including an inclusion body of nucleic acid; or an extracellular vesicle?". The determination result of "malaria-positive. Includes: a red blood cell including an inclusion body of nucleic acid; or an extracellular vesicle?" means that it can be determined that malaria-infected red blood cells are in the blood specimen to be analyzed, but it is difficult to determine that the blood specimen to be analyzed includes a red blood cell including an inclusion body of nucleic acid, or an extracellular vesicle.

Meanwhile, when the coefficient of variation is greater than or equal to the threshold value th23, the controller 51 determines "includes: a red blood cell including an inclusion body of nucleic acid; or an extracellular vesicle" in step S128, and causes the storage unit 52 to store the determination result. The controller 51 ends the determination process. In this case, the determination result is changed from "malaria-positive? and includes: a red blood cell including an inclusion body of nucleic acid; or an extracellular vesicle?" which has been stored in step S123 to "includes: a red blood cell including an inclusion body of nucleic acid; or an extracellular vesicle".

In step S128, the controller 51 may determine "malaria-positive? and includes: a red blood cell including an inclusion body of nucleic acid; or an extracellular vesicle". The determination result of "malaria-positive? and includes: a red blood cell including an inclusion body of nucleic acid; or an extracellular vesicle" means that it can be determined that the blood specimen to be analyzed includes a red blood cell including an inclusion body of nucleic acid, or an extracellular vesicle, but it is difficult to determine that malaria-infected red blood cells are included.

Figure 17:
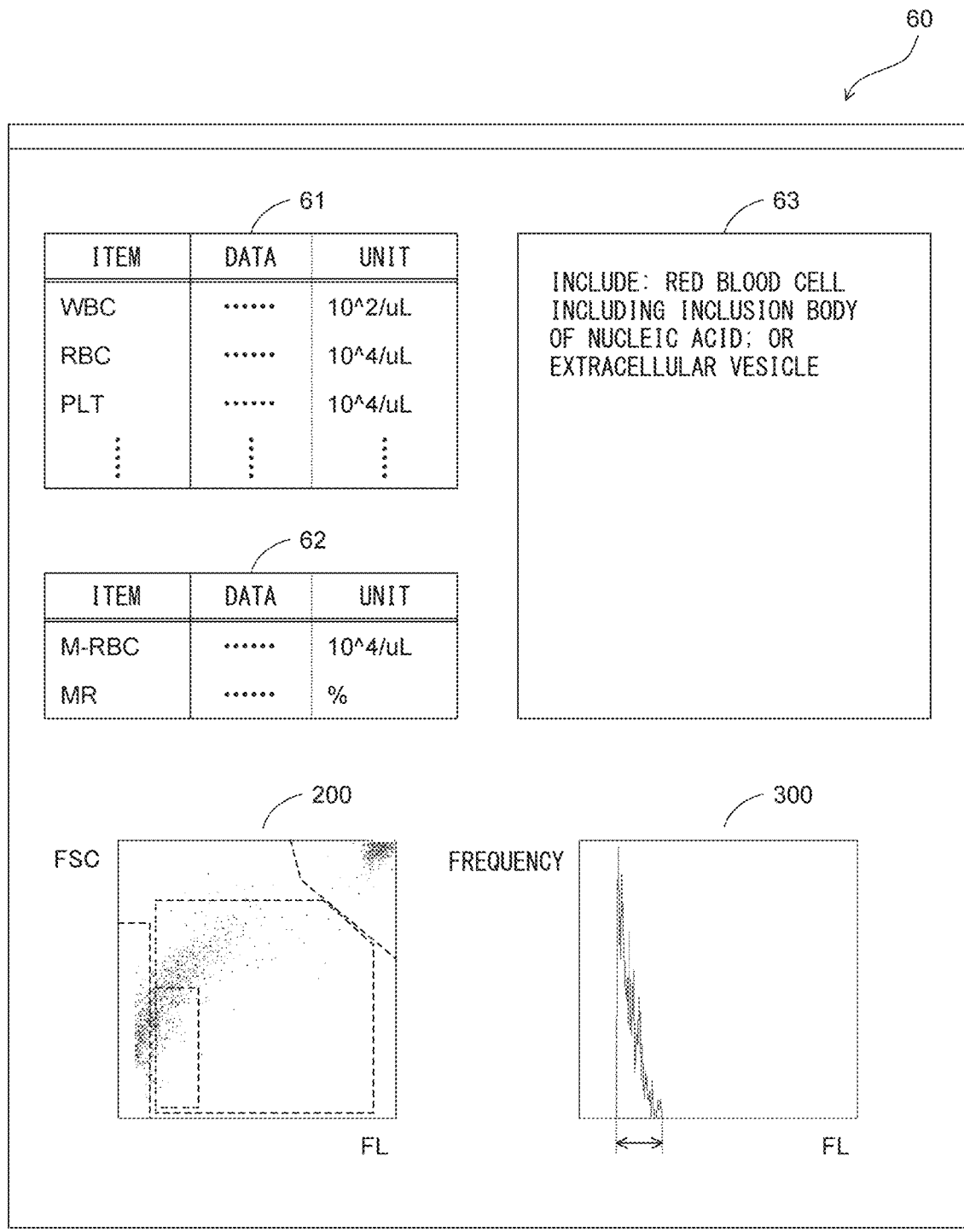
FIG. 17 is a schematic diagram illustrating a configuration of a screen displayed on the display unit according to Embodiment 2.

As shown in FIG. 17, also in Embodiment 2, the result of the determination process shown in FIG. 16 is displayed on the screen 60. The screen 60 of Embodiment 2 has the same configuration as the screen 60 of Embodiment 1 shown in FIG. 10.

Also in Embodiment 2, the determination result obtained in the determination process shown in FIG. 16 is displayed in the comment region 63. Specifically, in a case where step S122 in FIG. 16 is performed, "malaria-negative, and does not include: a red blood cell including an inclusion body of nucleic acid; and an extracellular vesicle" is displayed in the comment region 63. When determination of step S124 in FIG. 16 is NO, "malaria-positive? and includes: a red blood cell including an inclusion body of nucleic acid; or an extracellular vesicle?" is displayed in the comment region 63. In this case, "malaria-positive? an extracellular vesicle? a red blood cell including an inclusion body of nucleic acid?" may be displayed. When step S127 in FIG. 16 is performed, "malaria-positive" is displayed in the comment region 63. When step S128 in FIG. 16 is performed, "includes: a red blood cell including an inclusion body of nucleic acid; or an extracellular vesicle" is displayed in the comment region 63 as illustrated in FIG. 17.

In a case where "malaria-negative", "malaria-positive?", "malaria-positive", or the like is displayed in the comment region 63, a doctor or the like can make the same determination as in Embodiment 1. In a case where "includes: a red blood cell including an inclusion body of nucleic acid; or an extracellular vesicle?", "includes: a red blood cell including an inclusion body of nucleic acid; or an extracellular vesicle", "extracellular vesicle?", or "red blood cell including inclusion body of nucleic acid?" is displayed in the comment region 63, a doctor or the like can consider, for example, a predetermined disease that is likely to be associated with a red blood cell including an inclusion body of nucleic acid, or an extracellular vesicle, as a material for determining a condition of the subject. For example, in a case where the doctor or the like considers that a red blood cell including a Howell-Jolly body is present, the doctor or the like can estimate that, for example, function of a spleen reduces. In a case where the doctor or the like considers that a red blood cell including basophilic stippling is present, the doctor or the like can estimate lead poisoning, benzene poisoning, pernicious anemia, or the like. In this case, the doctor or the like may perform additional test such as checking of the blood specimen with the use of a microscope.

Embodiment 3

Figure 18:
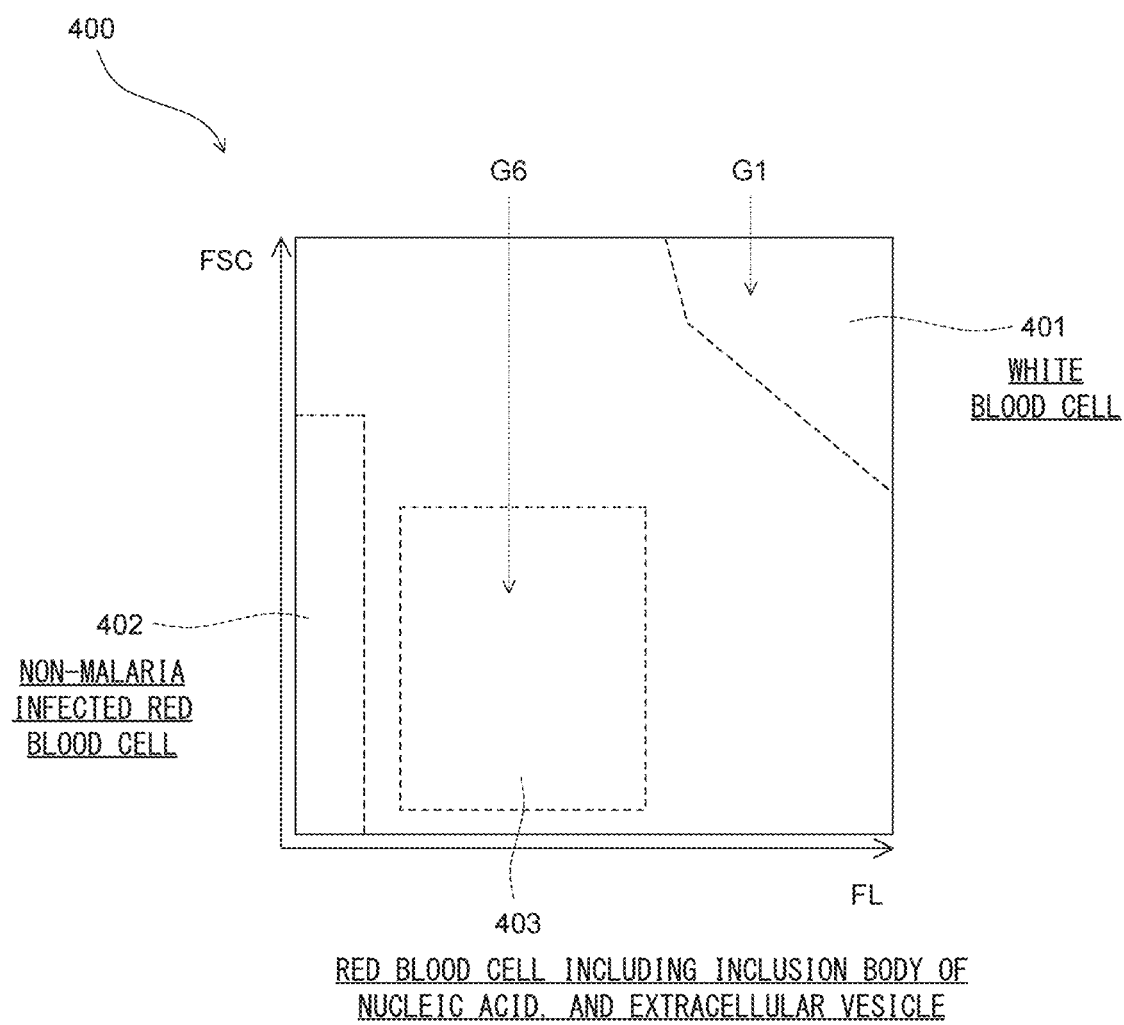
FIG. 18 is a schematic diagram illustrating a scattergram based on a first measurement according to Embodiment 3.
Figure 19:
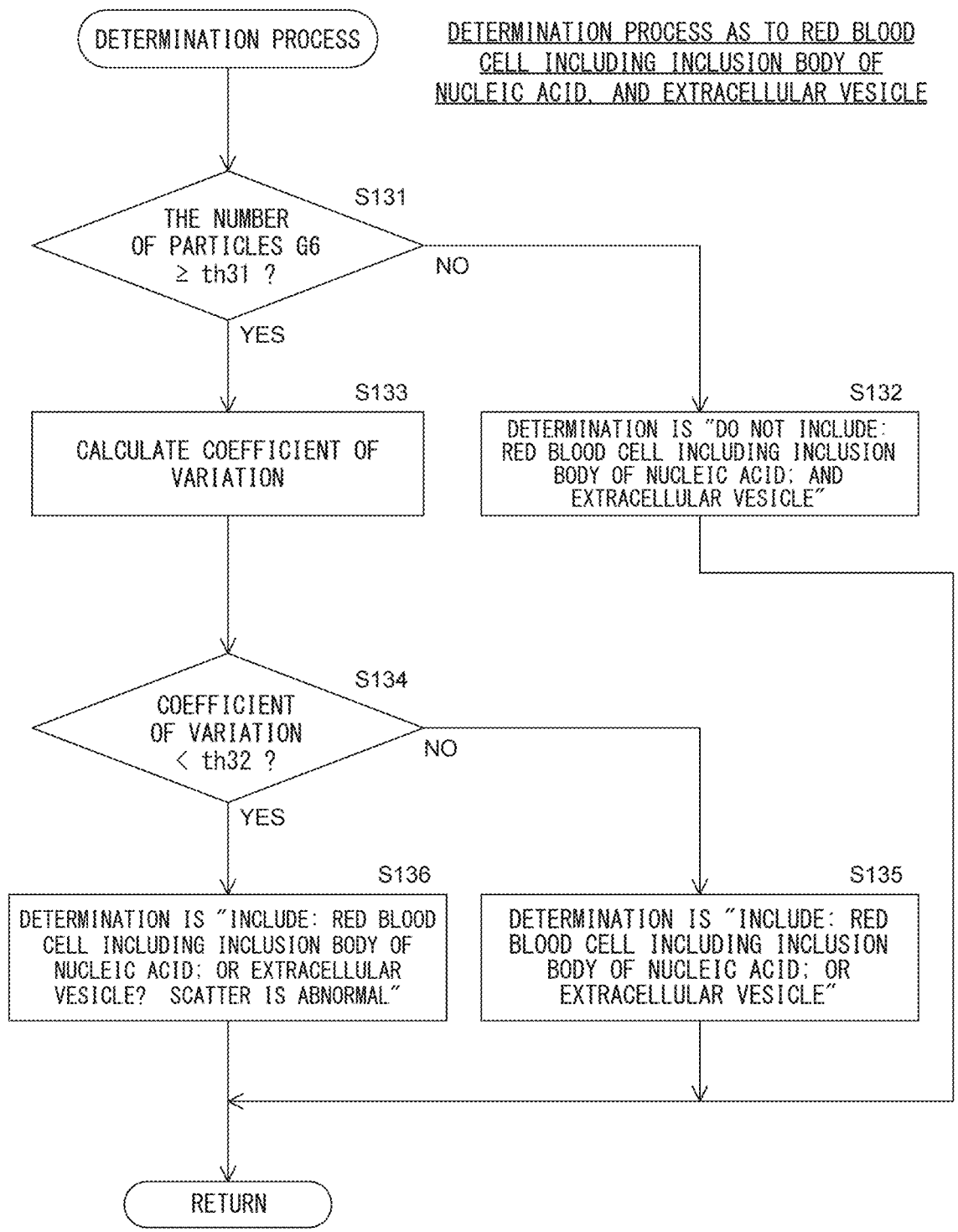
FIG. 19 is a flow chart showing a determination process as to a red blood cell including an inclusion body of nucleic acid, and an extracellular vesicle, according to Embodiment 3.

According to Embodiment 3, in the determination process, whether at least one of a red blood cell including an inclusion body of nucleic acid, and an extracellular vesicle is present or absent is determined. As described above, a red blood cell including an inclusion body of nucleic acid, or an extracellular vesicle may be distributed in the region 203 corresponding to malaria-infected red blood cells in the scattergram 200 in some cases. In Embodiment 3, as shown in FIG. 18, in a scattergram 400, a region 403 corresponding to a red blood cell including an inclusion body of nucleic acid, and an extracellular vesicle is provided. In Embodiment 3, the determination process is performed as shown in FIG. 19. The other configuration in Embodiment 3 is the same as for Embodiment 1.

As shown in FIG. 18, the axes in the scattergram 400 are the same as those in the scattergram 200. That is, in the scattergram 400, the vertical axis represents a forward scattered light intensity and the horizontal axis represents a fluorescence intensity.

In the scattergram 400, white blood cells are generally distributed in a region 401 corresponding to the region 201 in Embodiment 1. Non-malaria-infected red blood cells are generally distributed in a region 402 corresponding to the region 202 in Embodiment 1. A red blood cell including an inclusion body of nucleic acid, and an extracellular vesicle are each smaller than a white blood cell, and are stained by fluorescent dye since a nucleic acid component is included therein. Therefore, a red blood cell including an inclusion body of nucleic acid, and an extracellular vesicle are generally distributed in the region 403. The forward scattered light intensity in the region 403 is lower than that in the region 401 corresponding to white blood cells. The fluorescence intensity in the region 403 is higher than that in the region 402 corresponding to non-malaria-infected red blood cells, and lower than that in the region 401 corresponding to white blood cells. As shown in FIGS. 8A, 8B, FIGS. 9A, 9B, FIG. 12A, FIG. 13A, and FIG. 14B, a red blood cell including an inclusion body of nucleic acid, and an extracellular vesicle are distributed so as to overlap the region 204, of Embodiment 1, corresponding to the single-ring form of red blood cells. Therefore, the region 403 corresponding to a red blood cell including an inclusion body of nucleic acid, and an extracellular vesicle are set so as to overlap the region 204 described above.

The region 403 is merely required to be set such that a red blood cell including an inclusion body of nucleic acid, and an extracellular vesicle, which are distributed in the scattergram 400, are included in the region 403. Therefore, the region 403 is set to be slightly smaller than the region 203 of Embodiment 1.

In Embodiment 3, in the process step of step S102 shown in FIG. 5A, on the basis of the fluorescence intensity and the scattered light intensity in measurement data, the controller 51 counts red blood cells including inclusion bodies of nucleic acid, and extracellular vesicles, instead of malaria-infected red blood cells, the single-ring form of red blood cells, and the multi-ring form of red blood cells. Specifically, the controller 51 identifies particles G6 in a range where red blood cells including inclusion bodies of nucleic acid, and extracellular vesicles appear. In the scattergram 400, the range where red blood cells including inclusion bodies of nucleic acid, and extracellular vesicles appear corresponds to the region 403. The controller 51 counts the number of the identified particles G6, thereby obtaining the number of red blood cells including inclusion bodies of nucleic acid, and the number of extracellular vesicles. The number of white blood cells is obtained in the same manner as in Embodiment 1.

As shown in FIG. 19, in step S131, the controller 51 determines whether or not the number of the particles G6 per unit volume is greater than or equal to the threshold value th31. The number of the particles G6 per unit volume is obtained by, for example, dividing the obtained number of the particles G6 by a volume of the first measurement sample that flows through the flow cell 101 while the first information is obtained. The threshold value th31 is set such that it can be determined that a blood specimen to be analyzed "does not include: a red blood cell including an inclusion body of nucleic acid; and an extracellular vesicle" on the basis of the number of the particles G6 per unit volume. The threshold value th31 is set to, for example, 200.

In a case where the number of the particles G6 per unit volume is less than the threshold value th31, the controller 51 determines, in step S132, that the blood specimen to be analyzed "does not include: a red blood cell including an inclusion body of nucleic acid; and an extracellular vesicle", and causes the storage unit 52 to store the determination result. The controller 51 ends the determination process.

Meanwhile, in a case where the number of the particles G6 per unit volume is greater than or equal to the threshold value th31, the controller 51 calculates, in step S133, a value representing variation of the frequency distribution with respect to the fluorescence intensities of the particles G6. Specifically, in step S133, the controller 51 calculates the coefficient of variation of the frequency distribution with respect to the fluorescence intensities of the particles G6. The value, representing variation of the frequency distribution, calculated in step S133 may be the standard deviation, or a half-value width in the frequency distribution chart, as well as the coefficient of variation.

When the coefficient of variation is calculated in step S133, the controller 51 calculates the coefficient of variation by data processing based on a procedure similar to the procedure in which a frequency distribution chart is generated, without generating a frequency distribution chart. However, the procedure is not limited thereto, and the controller 51 may generate a frequency distribution chart and calculate the coefficient of variation. The controller 51 does not generate a frequency distribution chart in order to calculate the coefficient of variation. However, the controller 51 generates the frequency distribution chart when the screen described below is displayed on the display unit 53a, and the controller 51 causes the display unit 53a to display the generated frequency distribution chart.

In step S133, the controller 51 may calculate, for example, the coefficient of variation of the frequency distribution with respect to the fluorescence intensities of particles in a range from the minimum value of the fluorescent intensity to the maximum value of the fluorescent intensity in the horizontal axis direction of the region 403, instead of the coefficient of variation based on the particles G6. That is, in step S133, the controller 51 may calculate the coefficient of variation based on the particles of which the fluorescence intensities in the measurement data are in a predetermined range.

Subsequently, in step S134, the controller 51 determines whether or not the coefficient of variation calculated in step S133 is less than the threshold value th32. The threshold value th32 is set such that it can be determined that a blood specimen to be analyzed "includes: a red blood cell including an inclusion body of nucleic acid; or an extracellular vesicle", on the basis of the coefficient of variation. The width, in the horizontal axis direction, of the region 403 in Embodiment 3 is set to be greater than the width of the region 204, shown in FIG. 5B, corresponding to the single-ring form of red blood cells. Therefore, the threshold value th32 is set to be greater than the threshold value th13 in step S116 shown in FIG. 6. The threshold value th32 is set to, for example, 20%.

In a case where the blood specimen includes malaria-infected red blood cells, variation of the frequency distribution based on the particles G6 is small. In a case where the blood specimen does not include malaria-infected red blood cells, variation for the frequency distribution based on the particles G6 is great. Therefore, by determining, in step S134, whether the coefficient of variation is great or small, whether at least one of a red blood cell including an inclusion body of nucleic acid, and an extracellular vesicle is present or absent can be determined.

In a case where the coefficient of variation is greater than or equal to the threshold value th32, the controller 51 determines, in step S135, that the blood specimen to be analyzed "includes: a red blood cell including an inclusion body of nucleic acid; or an extracellular vesicle", and causes the storage unit 52 to store the determination result. The controller 51 ends the determination process. Meanwhile, in a case where the coefficient of variation is less than the threshold value th32, the controller 51 determines, in step S136, that the blood specimen to be analyzed "includes: a red blood cell including an inclusion body of nucleic acid; or an extracellular vesicle? scatter is abnormal", and causes the storage unit 52 to store the determination result.

The determination result of "includes: a red blood cell including an inclusion body of nucleic acid; or an extracellular vesicle?" means that the blood specimen to be analyzed is highly likely to include a red blood cell including an inclusion body of nucleic acid, or an extracellular vesicle, but it is difficult to determine that the blood specimen to be analyzed "includes: a red blood cell including an inclusion body of nucleic acid; or an extracellular vesicle". In this case, "scatter is abnormal" in the determination result is information representing reliability of the determination result as to presence or absence of at least one of a red blood cell including an inclusion body of nucleic acid, and an extracellular vesicle. Specifically, "scatter is abnormal" is information that indicates that reliability of the determination result as to presence or absence of at least one of a red blood cell including an inclusion body of nucleic acid, and an extracellular vesicle, is not high. The controller 51 ends the determination process. In a case where the coefficient of variation is less than the threshold value th32, malaria-infected red blood cells are highly likely to be present, and, therefore, the determination may be "malaria-positive".

In the determination process shown in FIG. 19, in a case where only blood specimens that do not include malaria-infected red blood cells are to be analyzed, steps S133, S134, S136 may be omitted. In this case, when the determination of step S131 is YES, the controller 51 determines, in step S135, that the blood specimen to be analyzed "includes: a red blood cell including an inclusion body of nucleic acid; or an extracellular vesicle".

Next, determination as to six kinds of specimens is specifically described with reference to FIG. 20A to FIG. 21D.

Figure 20A:
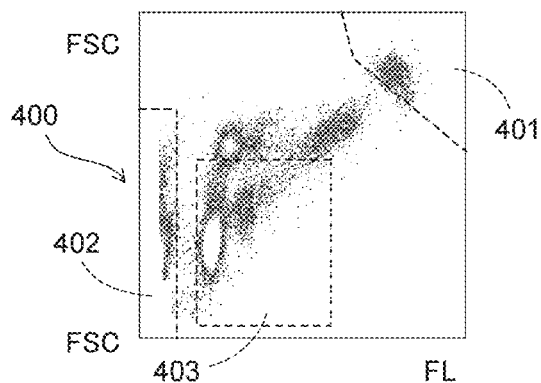
FIG. 20A illustrates a scattergram based on one specific kind of specimen, according to Embodiment 3.
Figure 20E:
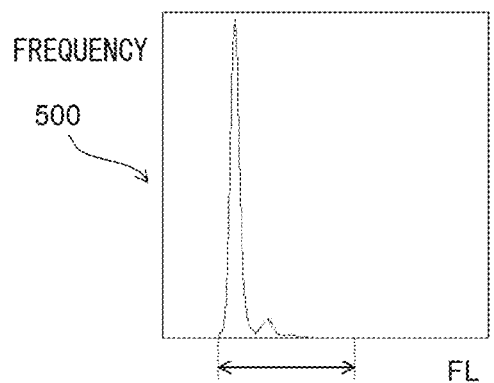
FIG. 20E illustrates a frequency distribution chart based on the one specific kind of specimen, according to Embodiment 3.
Figure 20B:
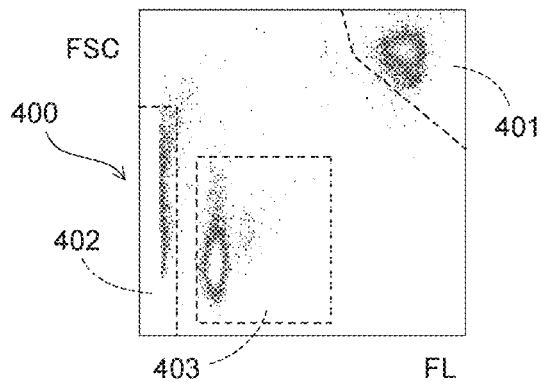
FIG. 20B illustrates a scattergram based on one specific kind of specimen, according to Embodiment 3.
Figure 20C:
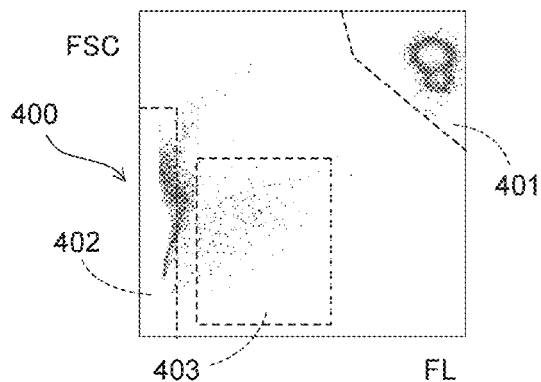
FIG. 20C illustrates a scattergram based on one specific kind of specimen, according to Embodiment 3.
Figure 20G:
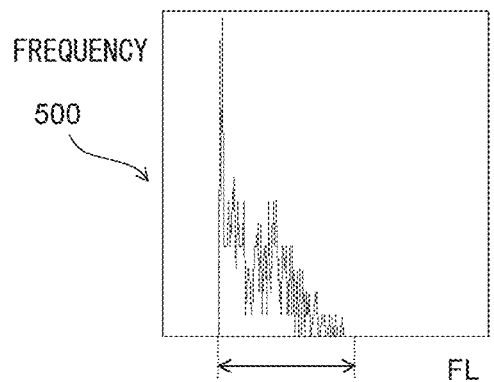
FIG. 20G illustrates a frequency distribution chart based on the one specific kind of specimen, according to Embodiment 3.
Figure 20D:
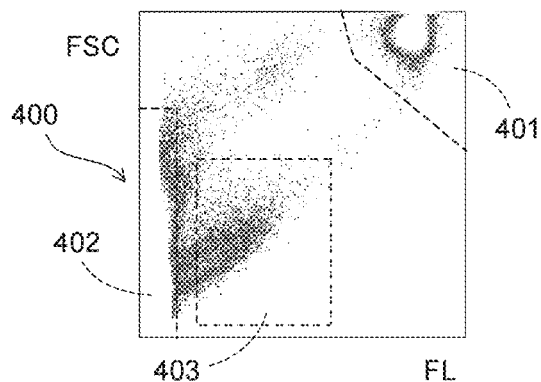
FIG. 20D illustrates a scattergram based on one specific kind of specimen, according to Embodiment 3.
Figure 20H:
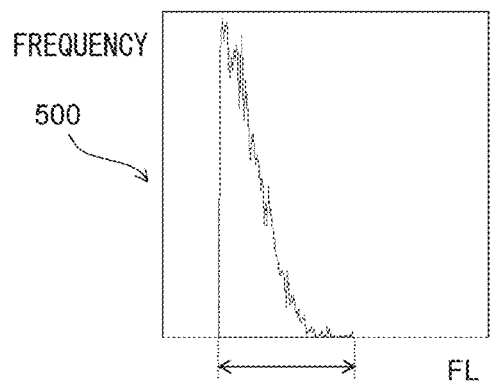
FIG. 20H illustrates a frequency distribution chart based on the one specific kind of specimen, according to Embodiment 3.
Figure 21A:
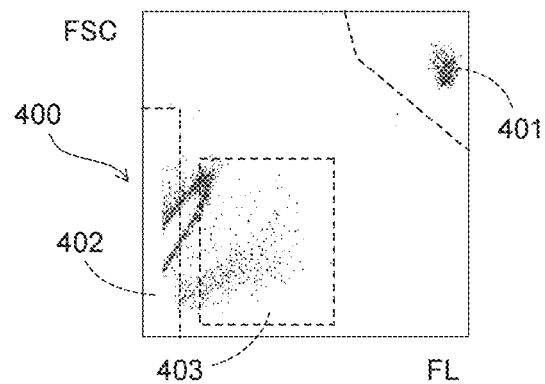
FIG. 21A illustrates a scattergram based on one specific kind of specimen, according to Embodiment 3.
Figure 21B:
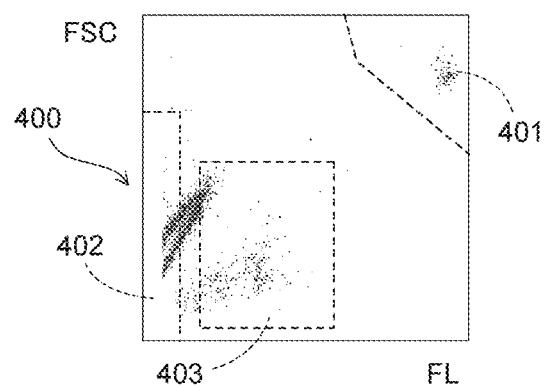
FIG. 21B illustrates a scattergram based on one specific kind of specimen, according to Embodiment 3.
Figure 21C:
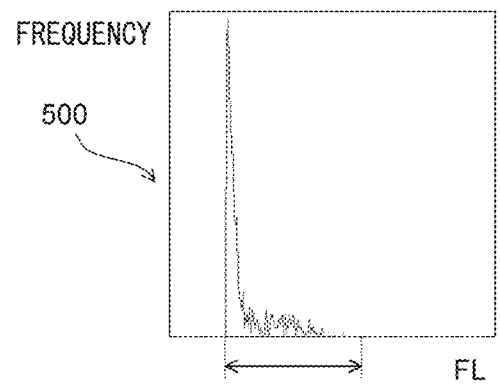
FIG. 21C illustrates a frequency distribution chart based on the one specific kind of specimen, according to Embodiment 3.
Figure 21D:
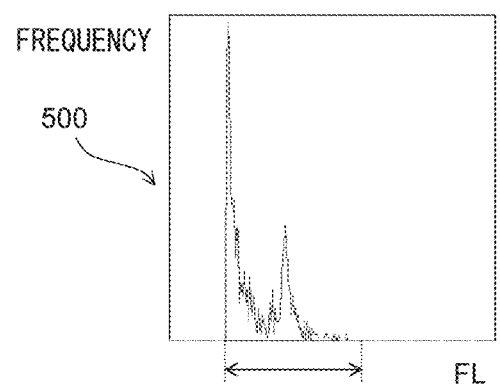
FIG. 21D illustrates a frequency distribution chart based on the one specific kind of specimen, according to Embodiment 3.

FIGS. 20A, 20B each show the scattergram 400 based on a blood specimen collected from a subject who suffers from malaria. FIGS. 20C, 20D each show the scattergram 400 based on a blood specimen collected from a subject who does not suffer from malaria. FIGS. 21A, 21B each show the scattergram 400 based on a blood specimen collected from a mouse that is not infected with malaria. In any case, particles at the left end of the region 402 are regarded as noise components, and eliminated.

In any of the six kinds of specimens shown in FIGS. 20A to 20D, FIGS. 21A, 21B, a certain number of particles appear in the region 403 corresponding to a red blood cell including an inclusion body of nucleic acid, and an extracellular vesicle. In FIGS. 20A to 20D, FIGS. 21A, 21B, the numbers of the particles G6 are 20134, 8273, 216, 5193, 1427, 573, respectively. Therefore, in the determination process shown in FIG. 19, determination of step S131 is YES, and the coefficient of variation of the frequency distribution with respect to the fluorescence intensities of the particles G6 is calculated in step S133.

FIGS. 20E to 20H, FIGS. 21C, 21D show frequency distribution charts 500 generated based on the scattergrams 400 in FIGS. 20A to 20D, FIGS. 21A, 21B, respectively. In each frequency distribution chart 500, the horizontal axis represents a fluorescence intensity, and the vertical axis represents frequency. The frequency distribution chart 500 indicates the frequency distribution based on only the particles G6 in a range where a red blood cell including an inclusion body of nucleic acid, and an extracellular vesicle appear. The frequency distribution chart 500 is normalized based on a value of the greatest frequency.

Figure 20F:
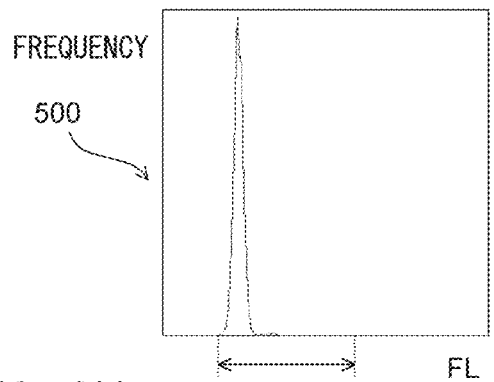
FIG. 20F illustrates a frequency distribution chart based on the one specific kind of specimen, according to Embodiment 3.

With reference to the frequency distribution chart 500 shown in each of FIGS. 20E, 20F, the frequency distribution forms a sharp shape in either case. The coefficients of variation in FIGS. 20E, 20F are 16.5%, 8.2%, respectively. Therefore, in either of the cases shown in FIGS. 20E, 20F, determination of step S134 in FIG. 19 is YES, and determination for the specimens is "includes: a red blood cell including an inclusion body of nucleic acid; or an extracellular vesicle?" scatter is abnormal". The specimens shown in FIGS. 20E, 20F are each a specimen infected with malaria as described above. Regardless of whether malaria-infected red blood cells are present or absent, both a case where the blood specimen includes a red blood cell including an inclusion body of nucleic acid, or an extracellular vesicle, and a case where the blood specimen does not include both a red blood cell including an inclusion body of nucleic acid, and an extracellular vesicle, can be considered. Therefore, in the determination process shown in FIG. 19, it can be understood that, for each of the two specimens, the determination result of "includes: a red blood cell including an inclusion body of nucleic acid; or an extracellular vesicle? scatter is abnormal" can be appropriately obtained, instead of the determination result which clearly indicates presence or absence of a red blood cell including an inclusion body of nucleic acid, or an extracellular vesicle.

Meanwhile, with reference to the frequency distribution chart 500 shown in each of FIGS. 20G, 20H, FIGS. 21C, 21D, the frequency distribution does not form a completely sharp shape in any case. The coefficients of variation in FIGS. 20G, 20H, FIGS. 21C, 21D are 26.5%, 22.3%, 30.8%, 32.0%, respectively. Therefore, in any of the cases shown in FIGS. 20G, 20H, FIGS. 21C, 21D, determination of step S134 in FIG. 19 is NO, and it is determined that these specimens each "include: a red blood cell including an inclusion body of nucleic acid; or an extracellular vesicle". The specimen shown in each of FIGS. 20G, 20H, FIGS. 21C, 20D is a specimen that is not infected with malaria. Therefore, it can be understood that, in the determination process shown in FIG. 19, these four specimens are not determined as "malaria-positive", and the determination result of "includes: a red blood cell including an inclusion body of nucleic acid; or an extracellular vesicle" can be appropriately obtained.

As described above, in the determination process shown in FIG. 19, in a case where a blood specimen includes a red blood cell including an inclusion body of nucleic acid, or an extracellular vesicle, and does not include a malaria-infected red blood cell, determination as "includes: a red blood cell including an inclusion body of nucleic acid; or an extracellular vesicle" can be appropriately made. In a case where a blood specimen includes a malaria-infected red blood cell, determination as "includes: a red blood cell including an inclusion body of nucleic acid; or an extracellular vesicle" is not made, and determination as "includes: a red blood cell including an inclusion body of nucleic acid; or an extracellular vesicle? scatter is abnormal" can be appropriately made.

Figure 22:
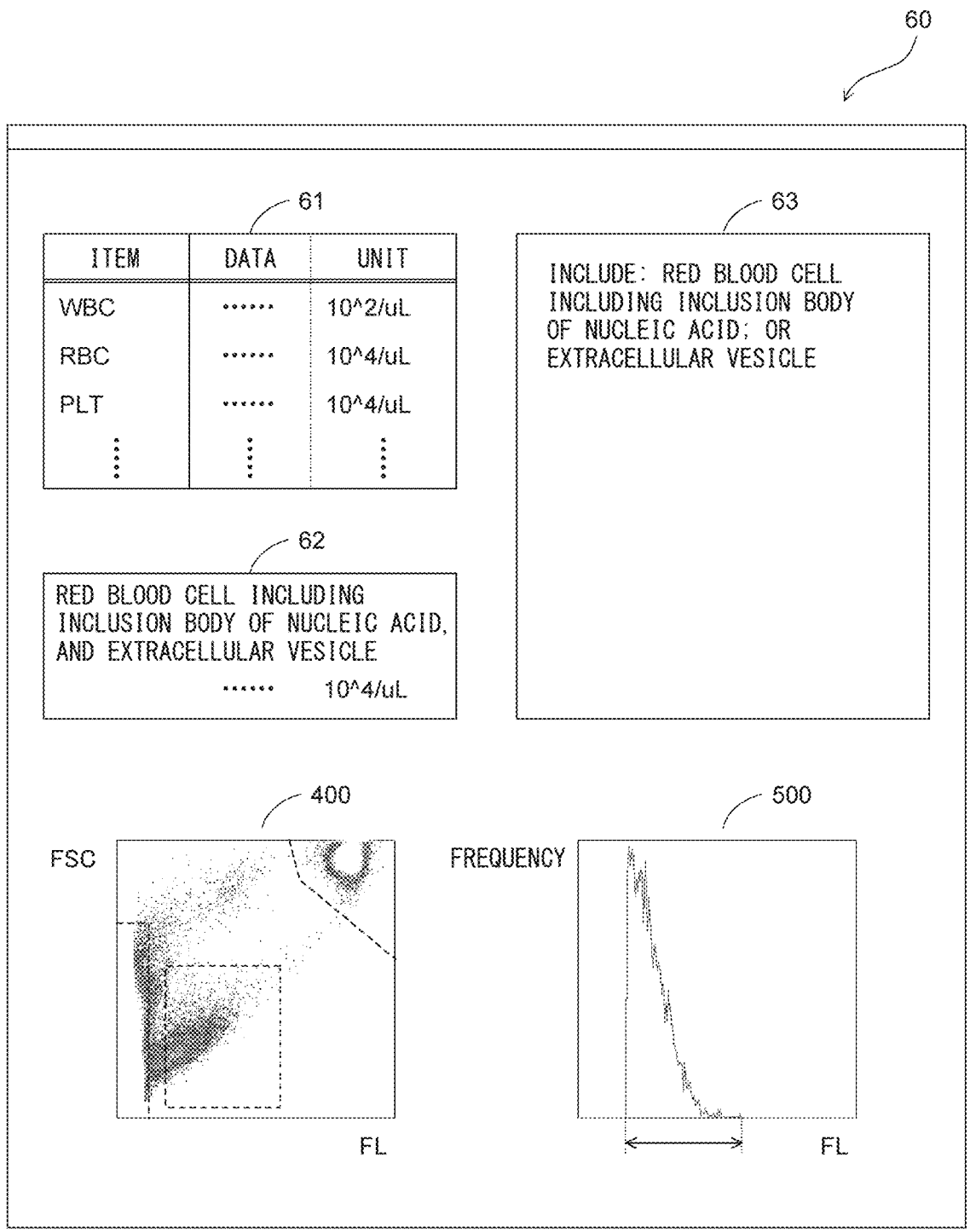
FIG. 22 is a schematic diagram illustrating a configuration of a screen displayed on the display unit according to Embodiment 3.
Figure 23:
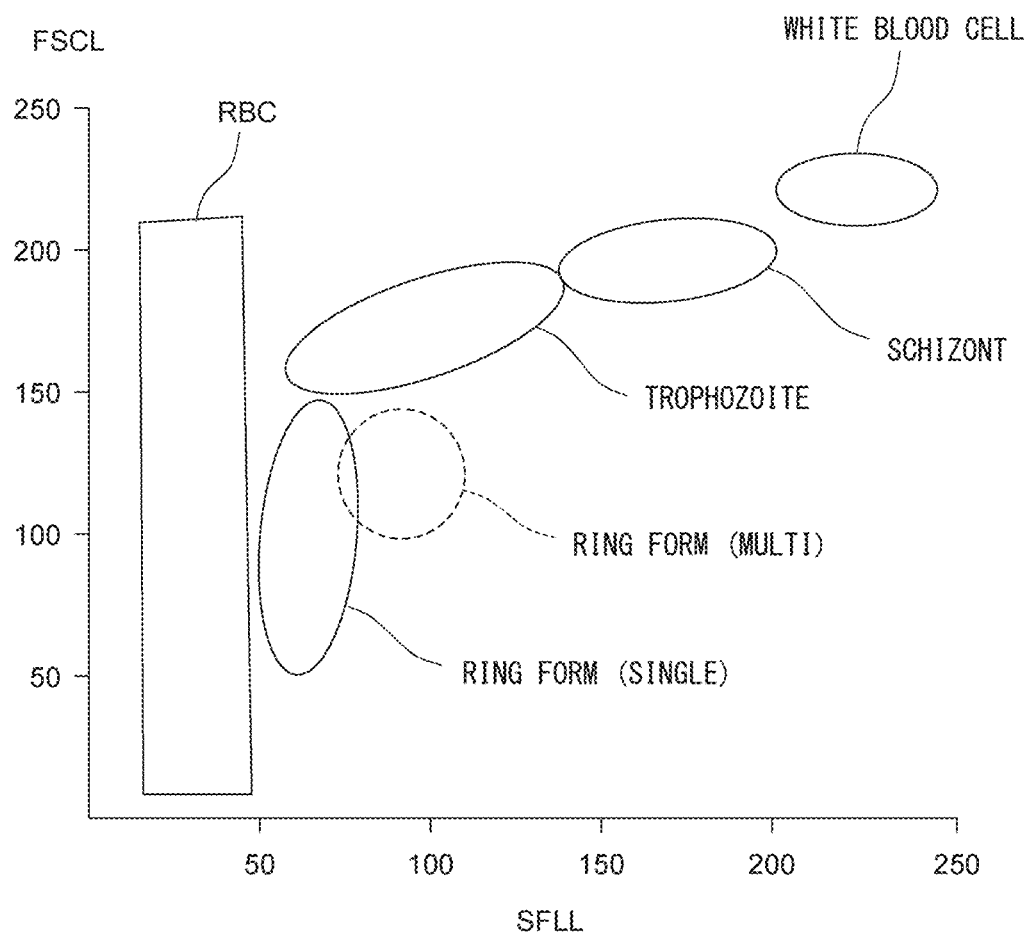
FIG. 23 is a schematic diagram illustrating a configuration of a scattergram in a related art.

As shown in FIG. 22, also in Embodiment 3, the result of the determination process shown in FIG. 19 is displayed on the screen 60. In Embodiment 3, in the list region 62, the result of counting of red blood cells including inclusion bodies of nucleic acid, and extracellular vesicles, that is, the result of counting of the particles G6 shown in FIG. 18, is displayed.

Also in Embodiment 3, the determination result obtained in the determination process shown in FIG. 19 is displayed in the comment region 63. Specifically, in a case where step S132 shown in FIG. 19 is performed, "does not include: a red blood cell including an inclusion body of nucleic acid; and an extracellular vesicle" is displayed in the comment region 63. In a case where step S136 shown in FIG. 19 is performed, "includes: a red blood cell including an inclusion body of nucleic acid; or an extracellular vesicle? scatter is abnormal" is displayed in the comment region 63. In this case, "extracellular vesicle? red blood cell including inclusion body of nucleic acid? scatter is abnormal" may be displayed. In a case where step S135 shown in FIG. 19 is performed, "includes: a red blood cell including an inclusion body of nucleic acid; or an extracellular vesicle" is displayed in the comment region 63 as illustrated in FIG. 22.

In a case where "includes: a red blood cell including an inclusion body of nucleic acid; or an extracellular vesicle?", "includes: a red blood cell including an inclusion body of nucleic acid; or an extracellular vesicle", "extracellular vesicle?", or "red blood cell including inclusion body of nucleic acid?" is displayed in the comment region 63, a doctor or the like can know that a blood specimen is likely to include a red blood cell including an inclusion body of nucleic acid, or an extracellular vesicle. As in Embodiment 2, the doctor or the like can consider, for example, a predetermined disease that is likely to be associated with a red blood cell including an inclusion body of nucleic acid, or an extracellular vesicle, as a material for determining a condition of a subject. The doctor or the like can perform additional test such as checking of the blood specimen with the use of a microscope.

In a case where "scatter is abnormal" is displayed in the comment region 63, a doctor or the like can know that reliability of the determination result as to presence or absence of at least one of a red blood cell including an inclusion body of nucleic acid, and an extracellular vesicle, is not high. In this case, the doctor or the like can know that particles, such as malaria-infected red blood cells, other than a red blood cell including an inclusion body of nucleic acid, and an extracellular vesicle may be distributed in the region 403 on the scattergram 400. By the scattergram 400 and the frequency distribution chart 500 being displayed on the screen 60, a doctor or the like can quickly know a state of the blood specimen in detail.

In Embodiments 2, 3, instead of whether or not at least one of a red blood cell including an inclusion body of nucleic acid, and an extracellular vesicle is present being determined, whether an extracellular vesicle is present or absent may be determined, or whether a red blood cell including an inclusion body of nucleic acid is present or absent may be determined. In this case, in Embodiments 2, 3, among a red blood cell including an inclusion body of nucleic acid, and an extracellular vesicle, display as to only the extracellular vesicle may be performed in the comment region 63, or display as to only the red blood cell including an inclusion body of nucleic acid may be performed in the comment region 63. In Embodiment 3, the result of counting of only extracellular vesicles may be displayed in the list region 62, or the result of counting of only red blood cells including inclusion bodies of nucleic acid may be displayed in the list region 62.

In Embodiments 2, 3, discrimination between an extracellular vesicle, and a red blood cell including an inclusion body of nucleic acid is not performed, and whether or not at least one of the two kinds of particles is included is determined. However, discrimination between these two kinds of particles may be performed and whether each of these two kinds of particles is present or absent may be determined. For example, in a case where the determination of step S134 in FIG. 19 is NO, whether an extracellular vesicle is present or absent and whether a red blood cell including an inclusion body of nucleic acid is present or absent may be further determined separately according to a value of the coefficient of variation or according to a distribution angle of the particles G6 in FIG. 18.

What is claimed is:

1. A blood analyzing method comprising:
   mixing a blood specimen and a fluorescent dye to prepare a measurement sample in which nucleic acids of Plasmodia parasitizing in red blood cells are stained;
   irradiating light to the measurement sample;
   detecting a fluorescence and a scattered light from individual cells in the measurement sample, caused in response to the irradiation; and
   plotting the individual cells on a coordinate plane having an axis of fluorescence intensity and an axis of scattered light intensity;
   counting cells plotted in a first region on the coordinate plane where malaria-infected cells are plotted;
   obtaining a value representing a variation of a distribution of cells appearing in a second region that is a narrowed part of the first region; and
   determining a Plasmodium infection as positive in response to determining that the value representing the variation of the distribution in the second region is less than a threshold value and the number of cells in the first region is greater than a threshold value.

2. The blood analyzing method of claim 1, wherein the second region is defined at a lower side with respect to both of the fluorescence intensity axis and the scattered light intensity axis, compared to the first region.

3. The blood analyzing method of claim 1, wherein the first region is defined to cover at least single-ring form and multi-ring form; and
   the second region is defined to cover at least single-ring form.

4. The blood analyzing method of claim 1, wherein the second region is defined by excluding a majority of the first region at an upper side with respect to the fluorescence intensity axis and the scattered light intensity axis.

5. The blood analyzing method of claim 1, wherein the value representing variation of distribution of particles appearing in the second region does not count non-malaria infected cells.

6. The blood analyzing method of claim 1, wherein the value representing the variation is obtained by translating the cells in the second region into a frequency distribution with respect to the fluorescence intensities.

7. The blood analyzing method of claim 1, wherein the value representing the variation is a coefficient of variation, a standard deviation, or a half-value width in a frequency distribution chart.

8. The blood analyzing method of claim 1, wherein the sample is additionally mixed with a diluent that causes red blood cells to contract.

9. The blood analyzing method of claim 1, wherein the light has a blue-violet wavelength band.

10. A blood analyzer comprising:
    a sample preparation unit comprising a reactor configured to mix a blood specimen and a fluorescent dye for staining a nucleic acid to prepare a measurement sample in which nucleic acids of Plasmodia parasitizing in red blood cells are stained;
    a light sensor configured to receive fluorescence and scattered light from individual cells in response to light irradiated onto the measurement sample; and
    a processor programmed to:
       plot the individual cells on a coordinate plane having an axis of fluorescence intensity and an axis of scattered light intensity;
       count cells plotted in a first region on the coordinate plane where malaria-infected cells are plotted;
       obtain a value representing a variation of a distribution of cells appearing in a second region that is a narrowed part of the first region; and
       determine a Plasmodium infection as positive in response to determining that the value representing the variation of the distribution in the second region is less than a threshold value and the number of cells in the first region is greater than a threshold value.

11. The blood analyzer of claim 10, wherein the second region is defined at a lower side with respect to both of the fluorescence intensity axis and the scattered light intensity axis, compared to the first region.

12. The blood analyzer of claim 10, wherein the first region is defined to cover at least single-ring form and multi-ring form; and the second region is defined to cover at least single-ring form.

13. The blood analyzer of claim 10, wherein the second region is defined by excluding a majority of the first region at an upper side with respect to the fluorescence intensity axis and the scattered light intensity axis.

14. The blood analyzer of claim 10, wherein the value representing variation of distribution of particles appearing in the second region does not count non-malaria infected cells.

15. The blood analyzer of claim 10, wherein the value representing the variation is obtained by translating the cells in the second region into a frequency distribution with respect to the fluorescence intensities.

16. The blood analyzer of claim 10, wherein the value representing the variation is a coefficient of variation, a standard deviation, or a half-value width in a frequency distribution chart.

* * * * *